United States Patent [19]

Cohen

[11] Patent Number: 5,027,816
[45] Date of Patent: Jul. 2, 1991

[54] HEMODYNAMICALLY RESPONSIVE SYSTEM FOR AND METHOD OF TREATING A MALFUNCTIONING HEART

[75] Inventor: Todd J. Cohen, San Francisco, Calif.

[73] Assignee: Leonard Bloom, Towson, Md.; a part interest

[21] Appl. No.: 416,276

[22] Filed: Oct. 2, 1989

Related U.S. Application Data

[63] Continuation-in-part of Ser. No. 233,367, Aug. 18, 1988, which is a continuation-in-part of Ser. No. 105,030, Oct. 6, 1987, Pat. No. 4,774,950.

[51] Int. Cl.$^5$ .............................................. A61N 1/00
[52] U.S. Cl. ........................ 128/419 PG; 128/419 D
[58] Field of Search ......... 128/419 P, 419 D, 419 PG

[56] References Cited

U.S. PATENT DOCUMENTS

| | | | |
|---|---|---|---|
| 4,730,619 | 3/1988 | Kouing et al. | 128/419 PG |
| 4,733,667 | 3/1988 | Olive et al. | 128/419 PG |
| 4,770,177 | 9/1988 | Schroeppel | 128/419 PG |
| 4,802,481 | 2/1989 | Schroeppel | 128/419 PG |
| 4,865,036 | 9/1989 | Chirifa | 128/a19 D |

Primary Examiner—Francis Jaworski
Assistant Examiner—George Manuel
Attorney, Agent, or Firm—Leonard Bloom

[57] ABSTRACT

A system for and method of treating a malfunctioning heart is based on hemodynamics, the pressure at a site in a patient's circulatory system being sensed. A signal is developed representative of short term mean arterial pressure (MAP) or right ventricular systolic pressure (RVSP), or right ventricular pulse pressure (RVPP). The rate of change and direction of the rate of change is determined and, if the rate of change in a given direction exceeds a predetermined amount, an indication of possible hemodynamic compromise, cardioversion/defibrillation is effected.

34 Claims, 34 Drawing Sheets

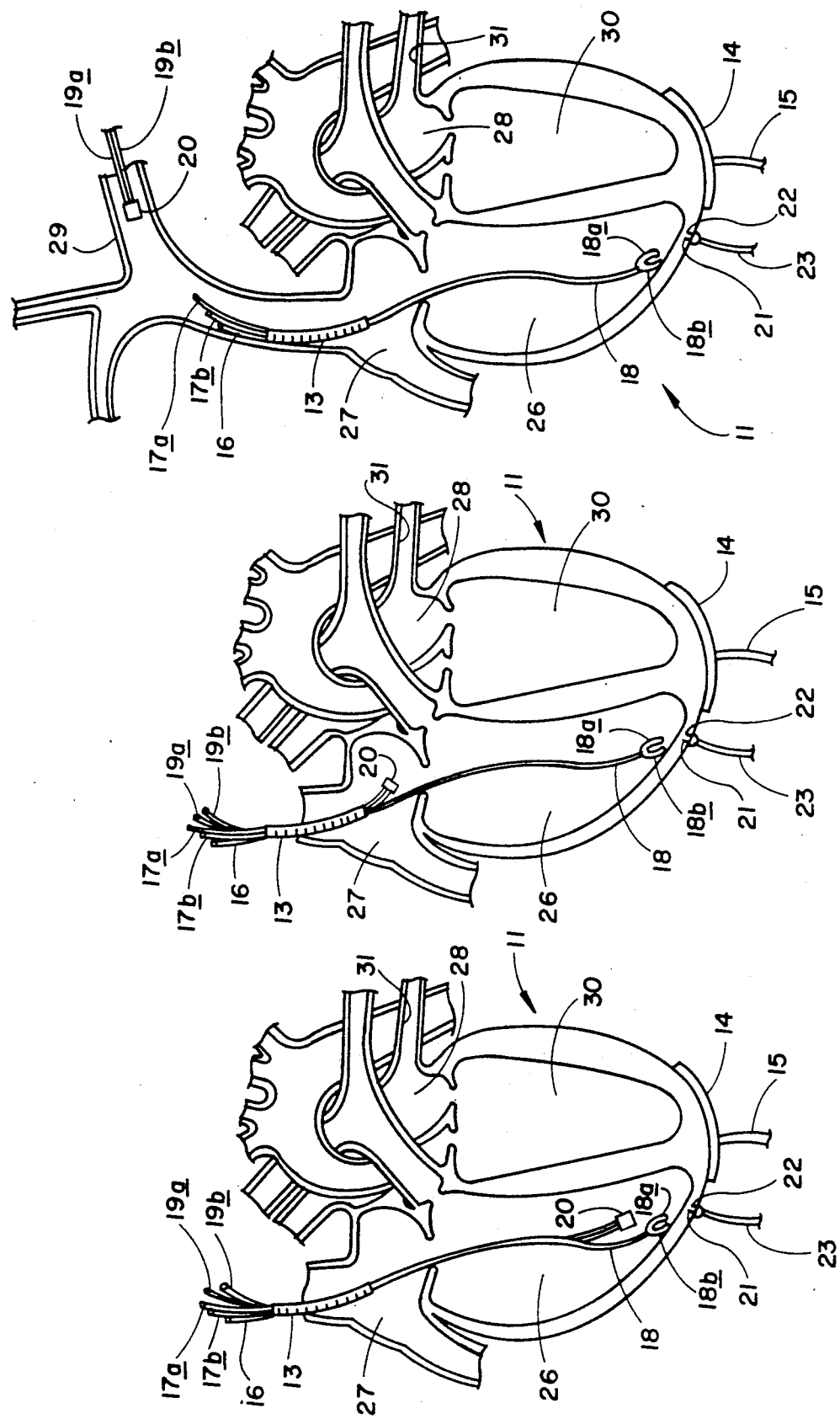

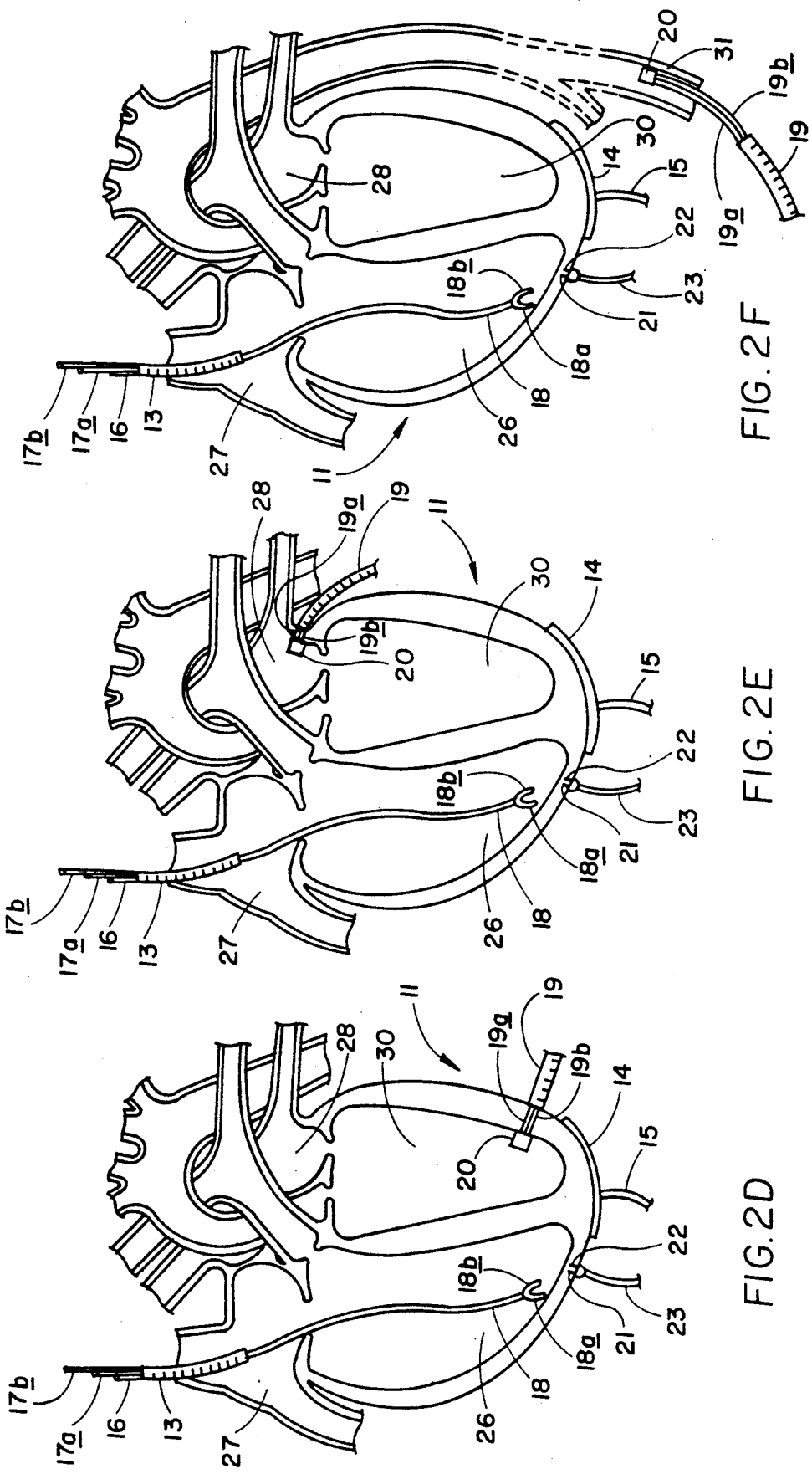

HEMODYNAMICALLY RESPONSIVE SYSTEM FOR AND METHOD OF TREATING A MALFUNCTIONING HEART

CROSS REFERENCE TO RELATED APPLICATION

This application is a continuation-in-part of copending application Ser. No. 233,367 of Todd J. Cohen filed Aug. 18, 1988 and entitled "Hemodynamically Responsive System for and Method of Treating a Malfunctioning Heart" which is a continuation-in-part of Ser. No. 105,030 of Todd J. Cohen filed on Oct. 6, 1987 and entitled "Hemodynamically Response System for and Method of Treating a Malfunctioning Heart", which has matured as U.S. Pat. No. 4,774,950 granted Oct. 4, 1988. The disclosures of the two prior applications are incorporated herein in their entirety respectively by reference.

BACKGROUND OF THE INVENTION

1. Field of the Invention

This invention relates to a system for and method of treating a malfunctioning heart and, more particularly, to such a system and method which effects cardioversion/defibrillation in response to sensing a heart malfunction. The term "hemodynamic parameter", as used herein, means any parameter which may be sensed or determined and either directly or indirectly affects the motion or constituents of blood or performance of the heart within the circulatory system. The invention provides for the cardioverting/defibrillation of a malfunctioning heart as well as the possibility of overcoming a tachycardia manifestation without resorting to either cardioverting or defibrillating the heart.

2. Description of the Prior Art

In recent years, substantial progress has been made in pacemakers and in the development of cardioverting-/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U.S. Pat. No. 3,942,536 of Mirowski et al., the technique involving responses to a sensed peak right ventricular systolic pressure dropping to a fixed predetermined threshold level. This known technique did not involve mean pressure changes in either direction from a baseline. Nor did it involve sensing of pressure within any vessels which extends between the heart and lung(s).

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators (AICD) which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. The AICD has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", Medical Instrumentation, Vol. 20, pages 285–291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", JACC, Vol. 6, No. 2, pages 461–466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One problem with current systems is that they function primarily as a rate-only sensing systems and may fire for nonmalignant as well as malignant tachycardias. These firings are not benign; potentially endangering myocardium, wasting energy and inflicting pain on the conscious patient, all distinct shortcomings and disadvantages.

SUMMARY OF THE INVENTION

The principal object of the present invention is to provide a system for cardioverting/defibrillating which avoids unnecessary firings, thereby reducing the danger to the myocardium, saving energy and avoiding pain.

Another object of the present invention is to provide an implantable system for cardioverting/defibrillating which avoids unnecessary firings, thereby reducing the danger to the myocardium, saving energy and avoiding pain.

A further object of the present invention is to provide a system for cardioverting/defibrillating which is hemodynamically responsive to the direction and the rate of change in a hemodynamic parameter, such as pressure, at a site in the circulatory system of a patient.

Yet another object of the present invention is to provide a method of cardioverting/defibrillating which may be advantageously carried out using a cardioverter-defibrillator constructed in accordance with the present invention.

Yet a further object of the present invention is to provide a method of cardioverting/defibrillating which avoids unnecessary firings thereby reducing the danger to the myocardium, saving energy and avoiding pain.

From one vantage point, the invention can be seen as being in a system for treating a malfunctioning heart of the type which includes storage means for storing electrical energy and electrode means for electrically coupling the storage means to the heart. Means are provided to determine at least one hemodynamic parameter. Means respond to output from the determining means and develop a first signal representing current level of the parameter over a period of given duration. Means responsive to the first signal determine rate of change of the first signal and algebraic sign of the rate of change. Means respond to output from the means responsive to the first signal are provided for charging and enabling discharge of the electrical energy stored by the storage means across the electrode means upon the rate of change of the first signal exceeding a predetermined magnitude in a given direction.

The means for developing the first signal representative of current level of the parameter may comprise means which provide a signal representative of current mean arterial pressure or current right ventricular systolic pressure or current right ventricular pulse pressure.

The responsive means may be realized as a microprocessor for developing a control signal to control the means for charging and enabling discharge of the electrical energy stored by the storage means.

Electrical means may be provided for sensing heart rate and producing a distinctive control signal upon the heart rate exceeding a predetermined rate. Controllable antitachycardia pacemaking means pacing signals to the heart. Controllable cardioverting/defibrillating means, including the storage means for storing electrical energy, are operatively associated with control circuit means which respond to the distinctive control signal and to an output from the means for charging and enabling discharge to enable the antitachycardia pacemaking means in response to presence of the distinctive control signal and contemporaneous absence of the output and for enabling the cardioverting/defibrillating means in response to contemporaneous presence of both the distinctive control signal and the output.

Means which respond to output from the electrical means for sensing heart rate and develop a discharge-synchronizing signal synchronized to an R-wave. The means for discharging electrical energy across the electrode means and into the heart, in this case, includes means for synchronizing the discharge with the discharge-synchronizing signal to effect cardioversion.

The means for discharging electrical energy across the electrode means and into the heart effects discharge on a nonsynchronized basis, in the absence of the synchronization signal, to effect defibrillation.

From a different viewpoint, the invention can be seen as being a method of treating a malfunctioning heart comprising providing a representation of a hemodynamic parameter, determining current level of the parameter over a period of given duration, determining rate of change and algebraic sign thereof in the current level, and delivering cardioverting/defibrillating electrical energy to the heart whenever the rate of change exceeds a predetermined amount in a given direction.

The step of determining may be determining pulse pressure at a site in the circulatory system of an individual or determining right ventricular pulse pressure or determining systolic pressure at a site in the circulatory system of an individual or by determining right ventricular systolic pressure or mean arterial pressure at a site in the circulatory system of an individual.

The method may include sensing heart rate, the step of delivering cardioverting/defibrillating electrical energy being taken upon the heart rate exceeding a given rate and the rate of change in the current level of the hemodynamic parameter exceeds the predetermined amount in the given direction.

The novel features that are considered characteristic of the invention in its method and system aspects are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

BRIEF DESCRIPTION OF THE DRAWINGS

FIG. 2A is an illustration of one catheter positioned within a heart, a pressure responsive sensor forming part of the catheter being shown positioned inside the right ventricle.

FIG. 2B is an illustration of a second catheter positioned within a heart, a pressure responsive sensor forming part of the catheter being shown positioned within the right atrium.

FIG. 2C is an illustration of a third catheter positioned within a major vein feeding into the superior vena cava or in the vena cava itself.

FIG. 2D is an illustration of a fourth catheter positioned within the left side of the heart, a pressure responsive sensor being shown positioned within the left ventricle.

FIG. 2E is an illustration of the fourth catheter positioned within the left side of the heart, a pressure responsive sensor a pressure responsive sensor being shown positioned within the left atrium.

FIG. 2F is an illustration of the fourth catheter positioned within the left side of the heart, a pressure responsive sensor being shown positioned at a point in the arterial system.

DETAILED DESCRIPTION OF THE PREFERRED EMBODIMENTS

Figure 1:
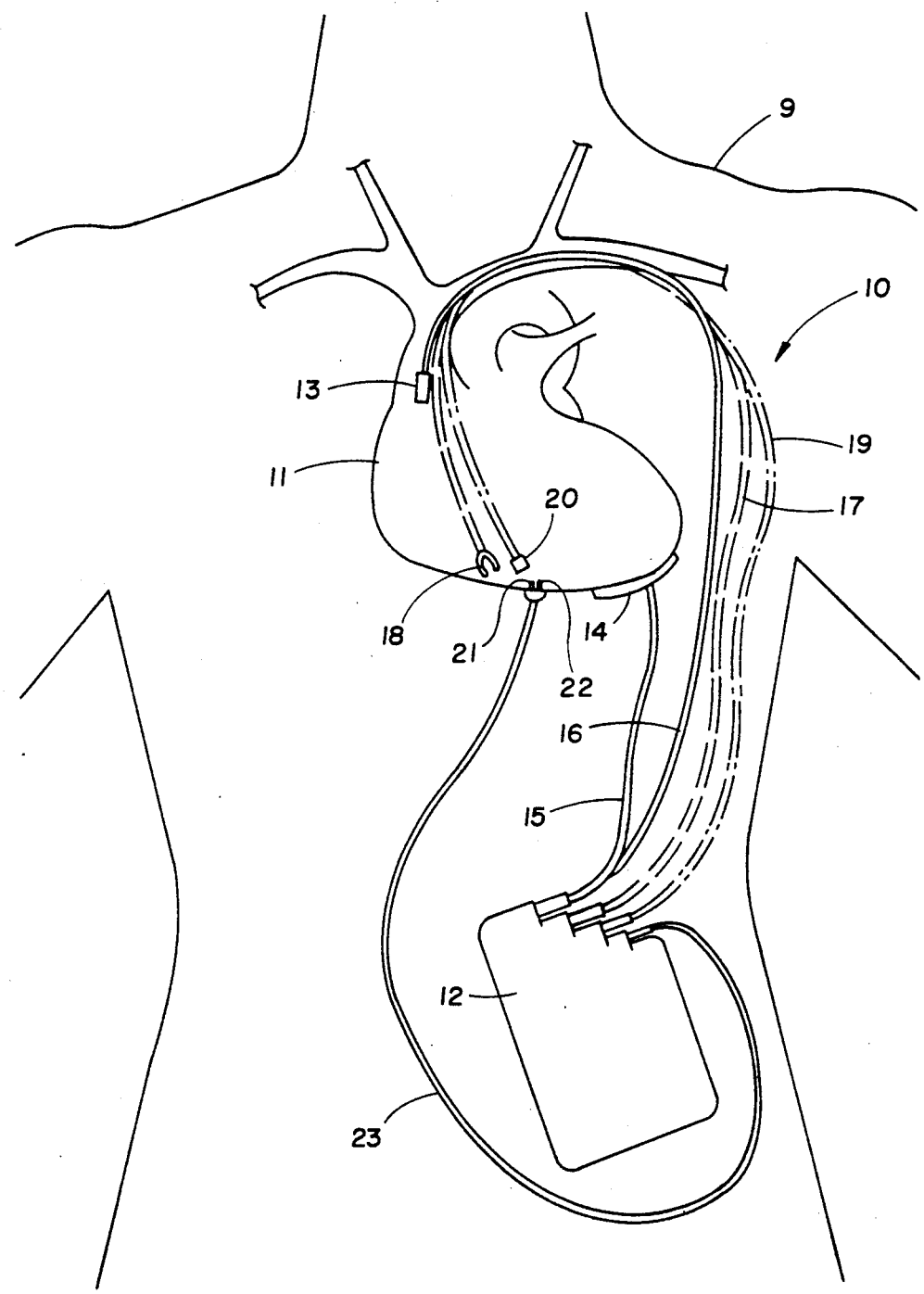
FIG. 1 is a diagrammatic, generalized illustration of an exemplary, implanted hemodynamically responsive system for treating a malfunctioning heart.

As shown in FIG. 1, an exemplary embodiment of an automatic implantable cardioverter-defibrillator system is designated generally by the numeral 10 and illustrated diagrammatically as being implanted within a human subject 9. The cardioverter-defibrillator system 10 includes an implanted housing 12 within which major circuit components of the system are housed. A first electrode 13 is positioned within the heart 11 of the subject 9, the details of placement and nature of the first electrode being more specifically shown in FIGS. 2A-2F and 2H-2J to which reference is to be made below. A second electrode, illustrated as a patch electrode 14 is positioned on the outside of the heart 11 at the apex thereof. The pair of electrodes 13, 14 are provided for the purpose of delivering D.C. cardioverting-/defibrillating energy from within the housing 12 to the heart 11 under control of circuitry within the housing, a pair of insulated leads 16 and 15 respectively being provided for this purpose. A pair of rate sensing electrodes 18 are provided within the heart 11, these electrodes being positioned in tissue and being conductively coupled to circuitry within the housing 12 via an insulated cable 17. A further pair of leads extend from a pressure responsive pressure-to-voltage transducer 20 to circuitry within the housing 12 via an insulated cable 19. It is to be understood that the insulated leads 15 and 16, the insulated cable 17 (or the pair of leads therein), and the insulated cable 19 (or the pair of leads therein) can all be incorporated into a single cable, the electrode 13, the rate sensing electrodes 18 and the pressure transducer 20 being carried by and forming parts of a catheter.

Pacemaking circuitry within the housing 12 may be provided to produce antitachycardia pacemaking signals, to a pair of pacing electrodes 21 and 22, illustrated as being fixed in tissue on the right-side of the heart. The pacing electrodes 21 and 22 are connected by respective conductive leads within a cable 23 which communicates with circuitry within the housing 12.

Turning to FIG. 2A, a more detailed illustration of the heart 11 of a subject, shows the heart in somewhat more detail and in section so that placement of parts of the system within the heart 11 can be seen in more detail, albeit diagrammatically. The heart 11 as illustrated includes a right ventricle 26, a right atrium 27, a left atrium 28 and a left ventricle 30. The electrode 13 is positioned within the superior vena cava. It is to be understood that the patch electrode 14, which cooperates with the electrode 13, could also be modified into a different form so it too could be positioned within the heart. The electrode 13 could be replaced with a patch electrode so that it also could be positioned on the surface of the heart, without departing from the present invention. The electrodes 13 and 14, in cases not involving implantation, could be replaced with conventional paddle electrodes or other external, body engaging electrodes, again without departing from the present invention. Thus, the invention could be used as a temporary measure for patient care in intensive care units and the like.

As illustrated in FIG. 2A, the pacing electrodes 21 and 22 are shown as being positioned on the exterior wall of right ventricle 26 for the purpose of illustration; these pacing electrodes could be placed elsewhere on or within the heart 11 in accordance with the needs of individual patients, taking into account the best particular location most suitable for correcting or overcoming the particular malfunction involved, the condition of the individual patient and his or her heart being taken into account.

Heart rate wave (R-wave) sensing electrodes 18a and 18b are illustrated as being positioned near the apex of the heart 11 within the right ventricle 26, for purposes of illustration. Other locations are equally well suited; again, the selected location being chosen with the condition of the particular patient and his or her heart in mind. The electrodes 18a and 18b are conductively connected to the circuitry within the housing 12 via leads 17a and 17b within the cable 17.

The pressure-to-voltage transducer 20, as illustrated in FIG. 2A, is positioned within the right ventricle 26. Two conductive leads 19a and 19b within the cable 19 (FIG. 1) provide electrical communication from the pressure responsive transducer 20 to circuitry within the housing 12 (FIG. 1). Thus, a D.C. voltage signal representative of the actual, instant pressure within the right ventricle 26 is fed to the circuitry within the implanted housing 12 (FIG. 1).

As illustrated in FIGS. 2B-2F and 2H-2J the heart 11, as well as the components of the system of the present invention, other than the pressure-to-voltage transducer 20, correspond to the heart 11 and the system components as shown in FIG. 2A. The placement of the transducer 20 differs, in each of FIGS. 2B-2F and 2H-2J. As shown in FIG. 2A, the transducer 20 provides, as its output, a variable D.C. voltage representative of the varying pressure within the right ventricle 26. As shown respectively in FIGS. 2B-2F and 2H-2J, the transducer 20 is positioned within and produces a variable D.C. voltage which represents respectively the pressure within the right atrium 27, within the central venous system (in particular, a major vein 29) the left ventricle 30, the left atrium 28, the arterial system (in particular, an artery 31 remote from the heart 11), a pulmonary artery, a pulmonary vein and a point to sense pulmonary capillary wedge pressure.

Figure 2G:
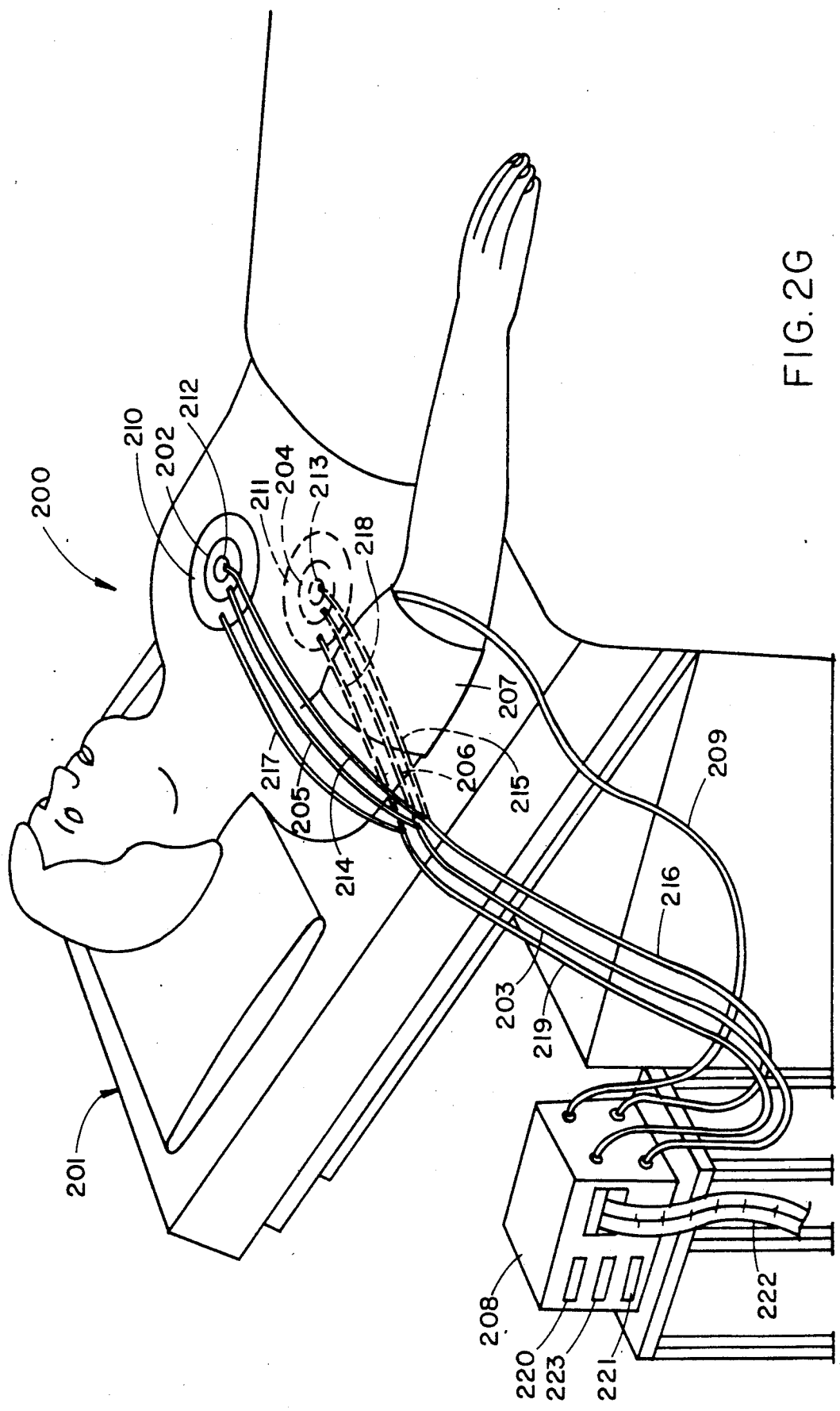
FIG. 2G is an illustration of a variant in which an external blood pressure cuff is provided to sense arterial pressure, from which MAP can be derived.
Figure 2I:
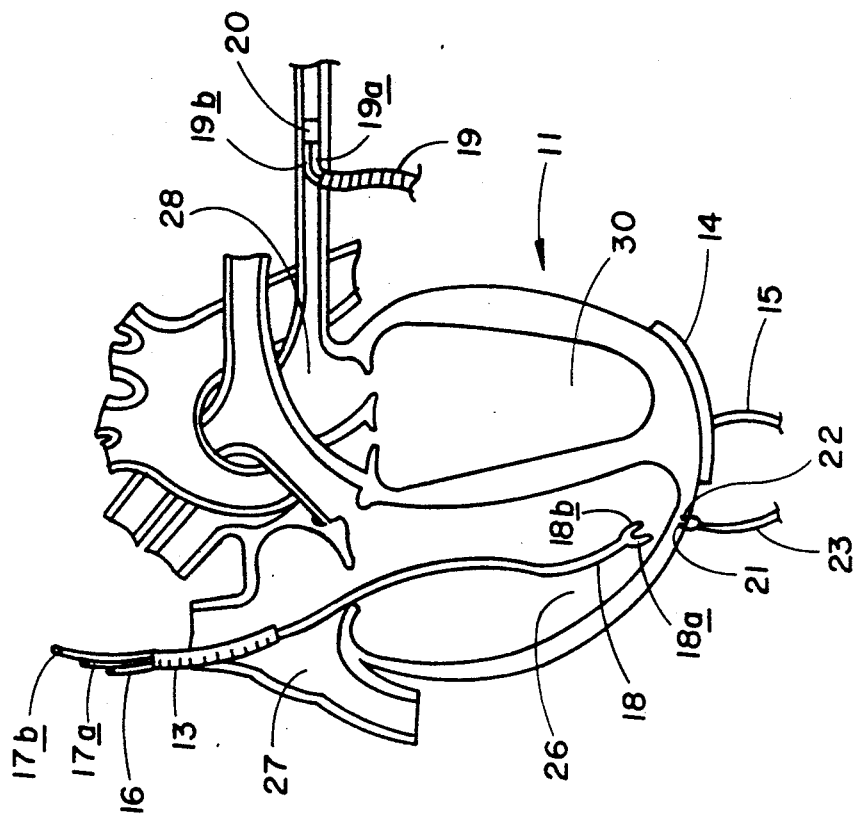
FIG. 2I is an illustration of a sixth catheter positioned within the left side of the heart, a pressure responsive sensor being positioned with a pulmonary vein between at least one lung and the heart.
Figure 2H:
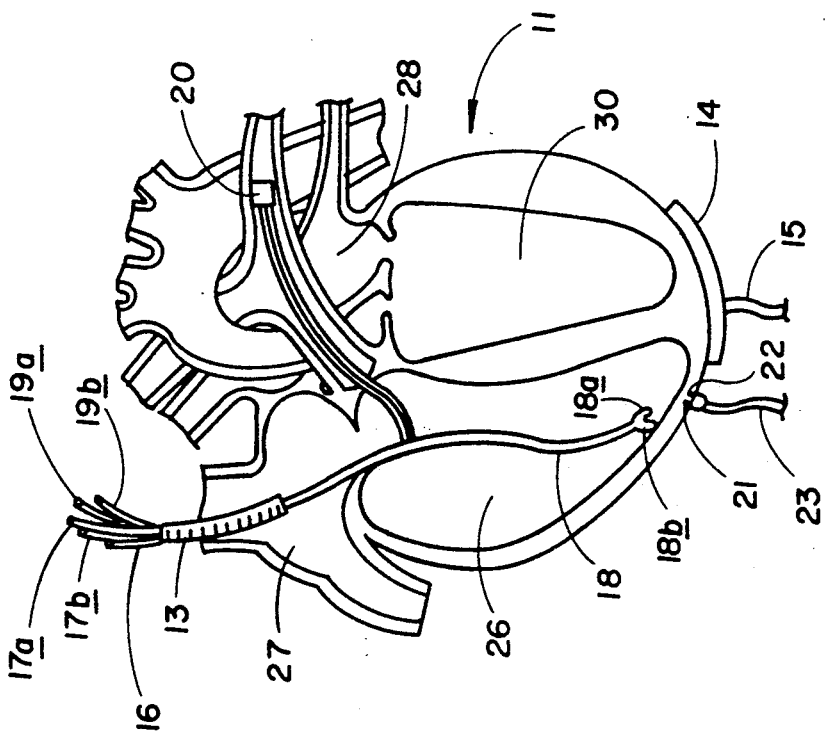
FIG. 2H is an illustration of a fifth catheter positioned within the left side of the heart, a pressure responsive sensor being shown positioned within a pulmonary artery between the heart and at least one lung.

In FIG. 2H, a fifth catheter is shown positioned in the right side of the heart. A pressure responsive sensor 20, in this case, is positioned in one of the pulmonary arteries extending toward one of the lungs. The sensor 20 could, if desired, be positioned more upstream in the layer pulmonary artery which carries blood to both lungs. The sensor 20 could be positioned in one of the smaller arteries which carries blood to one or another of the lobes of one lung. The other, components of the catheter fifth correspond to those illustrated in FIGS. 2A-2C.

It is also within the contemplation of the present invention to place the pressure sensor 20 within a pulmonary vein (feeding into left side of heart), as shown diagrammatically in FIG. 2I; in this case the conductive leads 19a, 19b and the cable 19 are positioned in the vicinity of the vein, with the leads 19a and 19b extending through the wall of the vein. In this case, the other components of the sixth catheter correspond to those of the catheters shown in FIGS. 2D-2F.

Figure 2J:
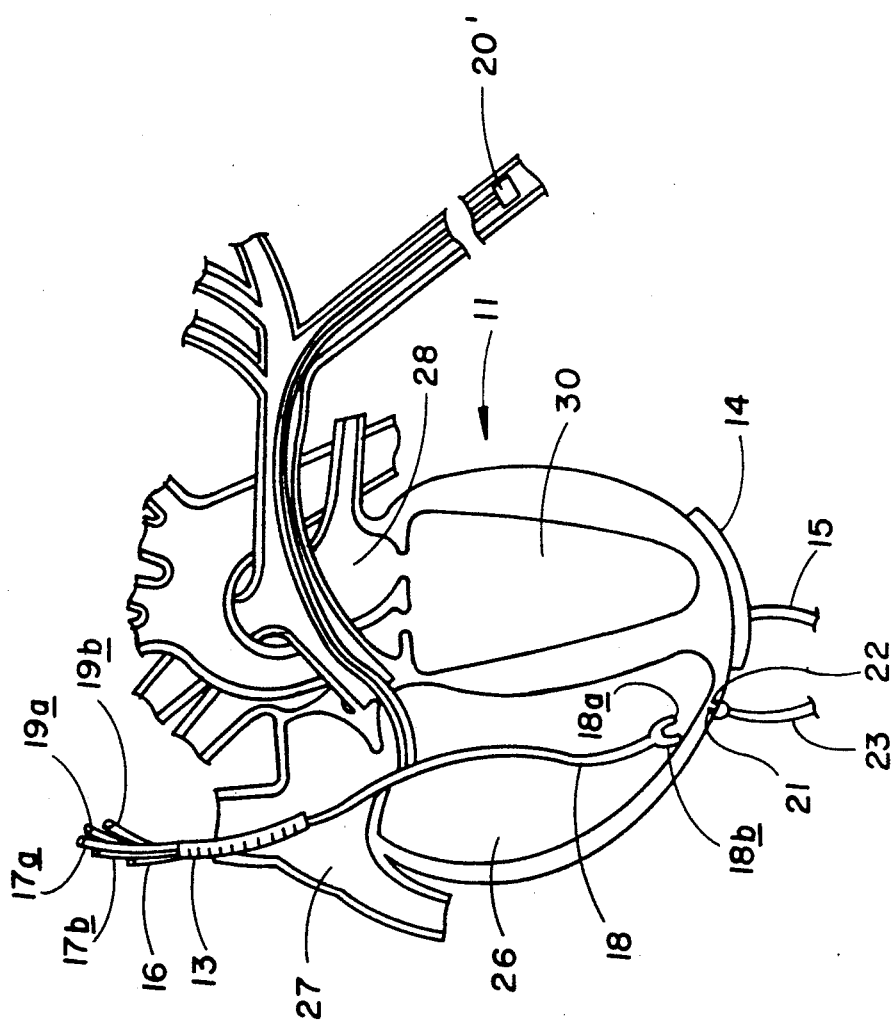
FIG. 2J is an illustration of a fifth catheter positioned within the left side of the heart, a pressure responsive sensor being positioned to effect sensing of pulmonary capillary wedge pressure.

Referring to FIG. 2J, as sensor 20' is shown positioned within a small blood vessel (being fed from a minor pulmonary artery) for the purpose of measuring pulmonary capillary wedge pressure. In a realized study conducted by applicant, pulmonary capillary wedge pressure was sensed using a dual lumen transvenous ballon tip catheter which was placed into the right heart chambers through the internal jugular vein and, thence, into the blood vessel. The other components of the catheter shown in FIG. 2J correspond to those shown in FIGS. 2H and 2I.

In FIG. 2G a portion of a noninvasive system for sensing heart rate and pressure of the type which may be used in an intensive care unit (ICU), a recovery room, coronary care unit (CCU), and/or in a routine care patient facility is illustrated. The system of FIG. 2G can be considered a system which can be substituted for the invasive systems shown in FIGS. 1, 2A-2F and 2H-2J. A patient 200 is shown in a reclined posture on a bed 201. A pair of pulse-delivering electrodes 202 and 204 (substitutes for electrodes 13, 14; FIGS. 2A-2F and 2H-2J) are positioned respectively on the anterior and posterior chest of the patient 200 for the purpose of coupling cardioverting/defibrillation energy pulses to the patient, respective insulated leads 205 and 206 (substitutes for leads 15, 16; FIGS. 2A-2F and 2H-2J) and a cable 203 being provided to conduct the pulses to the patient, from a pulse-generating apparatus 208 (substitute for the circuitry within housing 12; FIG. 1). The leads 205 and 206 and electrodes 202 and 204 are to be used in place of the cardioverting/defibrillating electrodes 13 and 14 (FIGS. 1, 2A-2F and 2H-2J), were the system of the present invention to be used in a noninvasive stand-alone or portable or patient-carried configuration, instead of in an implantable configuration as illustrated in FIGS. 1, 2A-2F and 2H-2J. Positioned concentrically about the respective electrodes 202 and 204 and insulated therefrom, are respective pacing electrodes 210 and 211 (substitutes for 21, 22; FIGS. 1, 2A-2F and 2H-2J). A pair of respective rate (R-wave) sensing electrodes 212 and 213 (substitutes for electrodes 18, FIG. 1; 18a, 18b, FIGS. 2A-2F and 2H-2J) are provided centrally within and insulated from the electrodes 202 and 204, respectively. The pair of rate-sensing electrodes 212, 213 are connected respectively via respective insulated leads 214, 215 and a cable 216 to the apparatus 208. The pair of pacing electrodes 210, 211 are connected respectively via respective insulated leads 217, 218 and a cable 219 to the apparatus 208.

Moreover, rather than an invasive pressure transducer of the type illustrated in FIGS. 1, 2A-2F and 2H-2J, the system may be modified to sense, in a noninvasive fashion, arterial pressure using a conventional cuff 207 removably fixed to, as shown, the right upper arm of the patient 200, the sensed pressure-related electrical signals being produced by a conventional transducer within the apparatus 207. A pneumatic tube or conduit 209 is provided both to supply automatically and intermittently compressed air to the cuff 207 and to receive either audible sounds (which are processed within the apparatus 208 to derive MAP representing data) or an electrical output from a transducer positioned within the cuff 207. The transducer produces electrical output signals which appears on a pair of conductive leads within the conduit 209. The cuff 207 is supplied, as is conventional, intermittently with compressed air via the air conduit 209. The components illustrated in FIG. 2G are used to monitor arterial blood pressure intermittently, for example once for a short period every 30 seconds. The pressure data so developed can be used to develop long-term mean baseline pressure-related signals and short-term (current) mean pressure-related signals. Such intermittently developed inputs can, as will be readily understandable by persons skilled in the art, be used in place of the inputs provided from the pressure sensing transducer 20 (FIGS. 1, 2A-2F and 2H-2J) to derive pressure- and heart rate-representing input signals for use in conjunction with the circuits discussed hereinbelow. The apparatus 208 may be provided with a heart rate display 220, baseline MAP display 221, and a current MAP display 223. An EKG strip recording 222 could be produced by the apparatus from a connection electrode arrangement (now shown) which could include the rate (R-wave) sensing electrodes 212 and 213. It is to be appreciated that the present invention can be realized using pressure transducers which may be implanted to sense arterial pressure. The pressure transducer may be arranged about a selected artery, for example.

Figure 3:
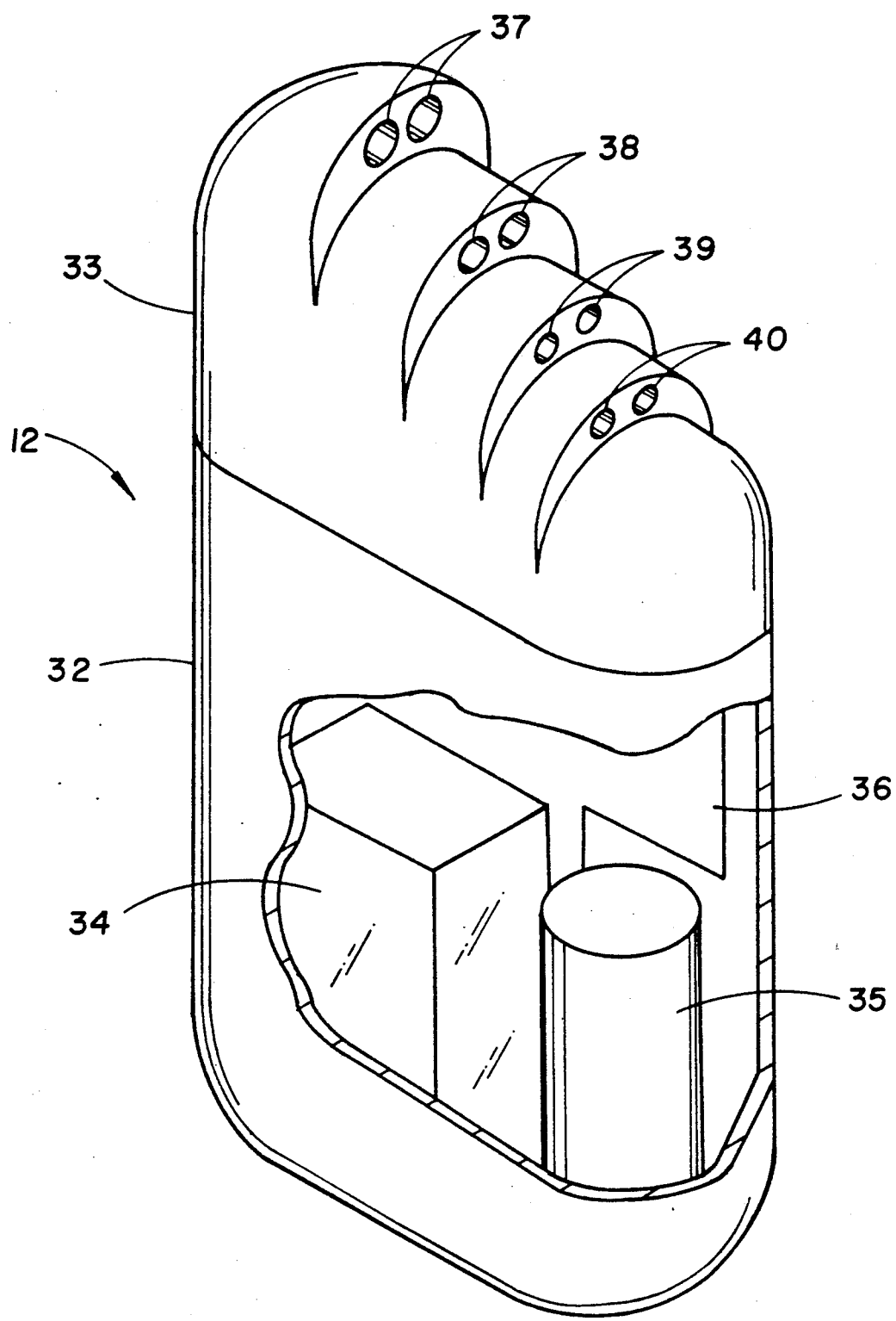
FIG. 3 is a pictorial illustration of an exemplary implantable controllable cardioverting/defibrillating electrical energy generator which may be used in practicing the present invention, the housing of the generator being partially broken away to show positioning of major components thereof.

One possible general implantable configuration of the housing 12 is shown in FIG. 3. The housing 12 includes a case 32, made of titanium, and a header 33, formed of an epoxy material, fixed to the case 32, all external components being hermetically sealed and biocompatible for human implantation. Within the case 32 is a battery pack or battery 34, an energy storage capacitor 35 and an electronic module 36 in or on which circuit components, other than the battery pack or battery 34 and the capacitor 35, are positioned. Detailed embodiments of exemplary circuits which are in or on or connected to the module 36 are illustrated in FIGS. 4, 6, 8 and 10, to which reference is made hereinbelow. A plurality of pairs of receptacles 37-40 are shown in the header 33 for receiving corresponding pairs of leads which are respectively within the insulated cables 15, 16 and 17 and 19 and 23 (FIG. 1).

Figure 4:
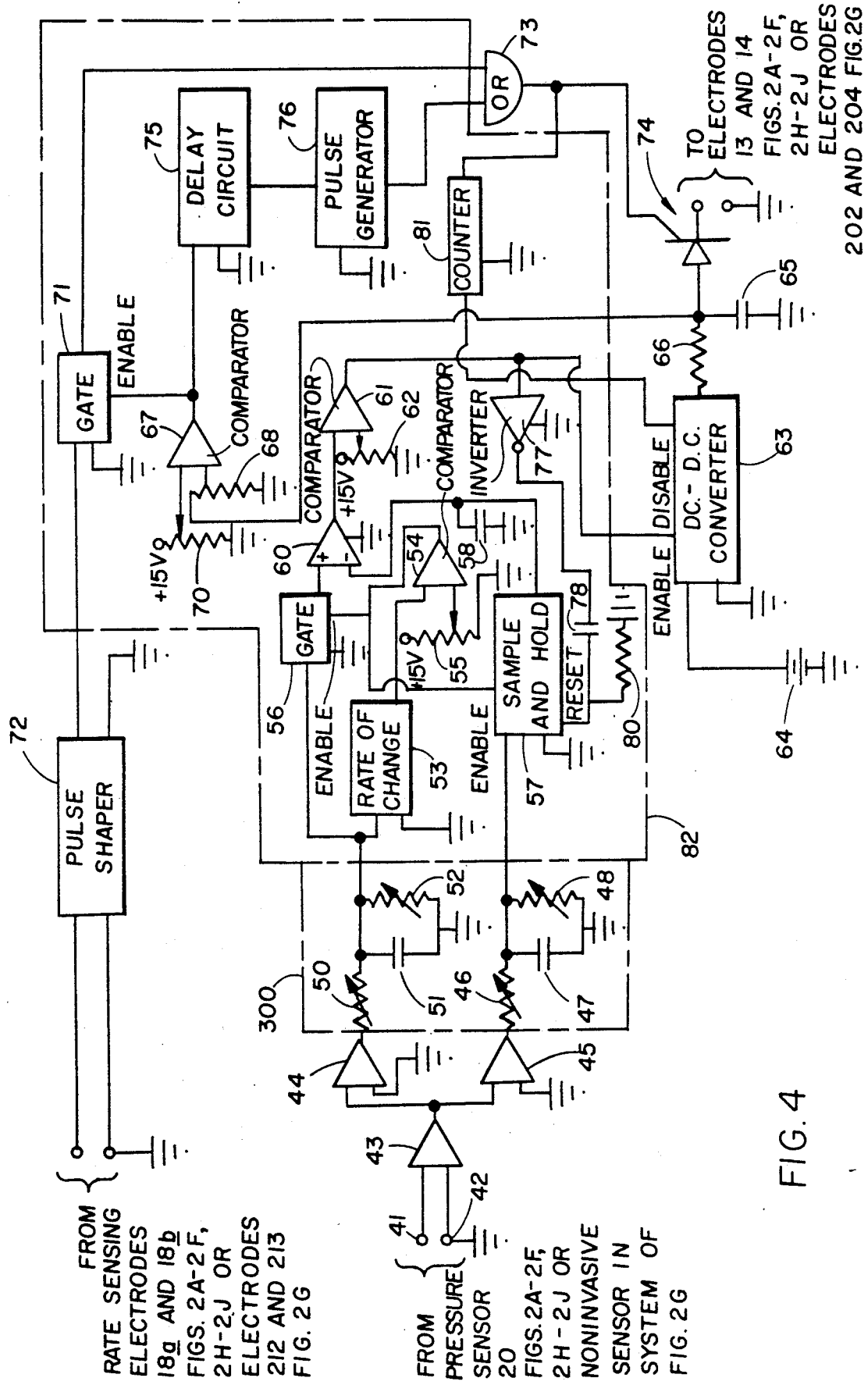
FIG. 4 is a partially block, schematic diagram of a hemodynamically responsive system for treating a malfunctioning heart which is pressure responsive.

Turning to FIG. 4, an exemplary embodiment of the circuit components, which may be positioned within the housing 12 (FIGS. 1 and 3) or the bed-side apparatus 208 (FIG. 2G), includes a pair of input terminals 41, 42 which receive the variable D.C. voltage output signal representing pressure from the pressure responsive transducer 20 (FIGS. 1, 2A-2F and 2H-2J) or noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 4 is suitable for treating a malfunction heart using a rate of change in current pressure-only criteria is used to initiate corrective action. It is to be understood that the portion of the circuitry designated 300 can be considered to be a signal processing circuit which may, in preferred embodiments, be replaced by the respective circuits shown in FIGS. 21-24.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage across the capacitor 47 represents the mean pressure sensed by the transducer 20 (FIGS. 1, 2A-2F and 2H-2J) or a noninvasive transducer (in system of FIG. 2G) over a relatively long period, for example during the preceding fifteen (15) minutes or even longer (for example a number of hours) or shorter (for example one hundred twenty (120) seconds) being suitable in some cases. The resistors 46 and 48 may be set by a medical professional to suit the particular patient involved, so far as what the most suitable period length (period of predetermined length) for baseline data acquisition appears to be most suitable. The D.C. voltage (first signal) which appears across the capacitor 47 thus represents a long term mean baseline pressure. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds). The resistors 50 and 52 may be set by a medical professional to suit the particular patient involved, so far as what the most suitable period length (period of given length) for current data acquisition appears to be most suitable.

As illustrated the long term (baseline) and short term (current) D.C. voltage signals which appear across the respective capacitors 47 and 51 are fed respectively to the input of a sample-and-hold circuit 57 and to the input of a rate-of-change determining circuit 53. The D.C. voltage signal, which appears as the output from the rate-of-change determining circuit 53, is directly proportional to the rate-of-change of a given algebraic sign of the current pressure sensed by the sensor 20 or the noninvasive sensor (FIG. 2G). Were the sensed pressure to be mean arterial pressure (MAP) or right ventricle systolic pressure (RVSP) or right ventricle pulse pressure (RVPP), the slope (direction) of the rate-of-change would be negative. The D.C. output signal from the determining circuit 53 is fed to a first input terminal of a first comparator 54, the second input terminal of the comparator 54 is connected to the wiper of a potentiometer 55 which is connected between ground and a point of fixed D.C. potential, illustrated as being +15 volts, from an internal power supply bus.

Whenever the voltage supplied to the comparator 54 from the determining circuit 53 exceeds the voltage supplied via the wiper from the potentiometer 55—an indication of rapid drop in pressure at a site in the circulatory system and possible hemodynamic compromise, a low (ZERO) level on the output terminal from the comparator 54 goes high (ONE). The ONE signal from the comparator 54 is coupled as an enabling input to a gate 56 and to a sample-and-hold circuit 57 which receive, at their respective signal input terminals, the voltage representing current mean pressure appearing across the capacitor 51 and the voltage representing mean baseline pressure appearing across the capacitor 47.

A D.C. output from the sample-and-hold circuit 57 is stored in a storage circuit, for the purpose of illustration shown as a capacitor 58. This stored voltage signal (stored first signal) representing mean baseline (long-term) pressure is supplied to the inverting input terminal of an operational amplifier 60 which has its noninverting input terminal connected to the output terminal of the gate 56, which when enabled, passes the D.C. voltage signal appearing across the capacitor 51 and representing current (short-term) mean pressure to the operational amplifier 60. As illustrated, the inverting and noninverting terminals of the operational amplifier 60 are shown as they would be connected were the hemodynamic parameter expected to increase. Were the hemodynamic parameter selected expected to drop—as would be the case were MAP, RVSP or RVPP to be the selected hemodynamic parameter, the terminals would be reversed. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of continuing hemodynamic compromise, the output terminal of the comparator 61 goes from low (ZERO) to high (ONE) which signal is passed to the enable terminal of a D.C.-to-D.C. converter 63. It is to be understood that the wipers of the potentiometers 55 and 62 are independently adjustable. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse is a truncated exponential pulse of about 25 Joules delivered approximately 17 seconds from onset of the hemodynamic compromise. The pulse could, especially when defibrillation is being undertaken after a failed attempt to cardiovert, be delivered somewhat later and with a higher energy level.

Once the capacitor 65 is charged to a sufficiently high D.C. voltage level to provide sufficient energy to effect cardioversion, as determined by a comparator 67, which receives on one input terminal a voltage proportional to the increasing D.C. voltage across the capacitor 65, a highly resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or from the rate sensing electrodes 212, 213 (FIG. 2G) and produces a pulse train in synchronism with the R-wave supplied from the electrodes 18a, 18b or electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy then stored on the capacitor 65 into the malfunctioning heart, via the electrodes 13 and 14 (FIGS. 1, 2A-2F and 2H-2J) or the electrodes 202 and 204 (FIG. 2G) in an effort to effect cardioversion, the discharge being in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more and enables a pulse generator 76 causing it to produce an output pulse to initiate defibrillation which is supplied, via the OR circuit 73, to the gate electrode of the SCR 74 causing the SCR to fire. The energy storage capacitor 65, which by then has charged to a higher level discharges, via the SCR 74 and the electrodes 13 and 14 (FIGS. 1, 2A–2F and 2H–2J) or the electrodes 202 and 204 (FIG. 2G), into the malfunctioning heart in an effort to effect defibrillation, the energy level being higher than would have been the case had the capacitor been discharged three seconds earlier. The delay circuit may be composed of an RC circuit connected to the comparator 67 so that the capacitor thereof charges toward the ONE level slowly; for example the capacitor may take about three (3) seconds or more as indicated above to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the stored signal representing baseline mean pressure and the signal representing current mean pressure returns to an acceptable level, indicating that the hemodynamic compromise has been overcome. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure (which would cause the output of the comparators 54 and 61 to become ZERO, removing the enable signals from the sample-and-hold circuit 57 and the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. An internal timer within the converter 63 holds the converter OFF for a given period so that the patient will not receive more shocks during this given period. At the end of the period the converter 63 returns to a READY condition and is again able to respond to an ENABLE signal from the comparator 61. The counter 81 resets itself to zero whenever it either reaches its maximum count of four or fails to reach the count of four within the given time period.

Figure 5A:
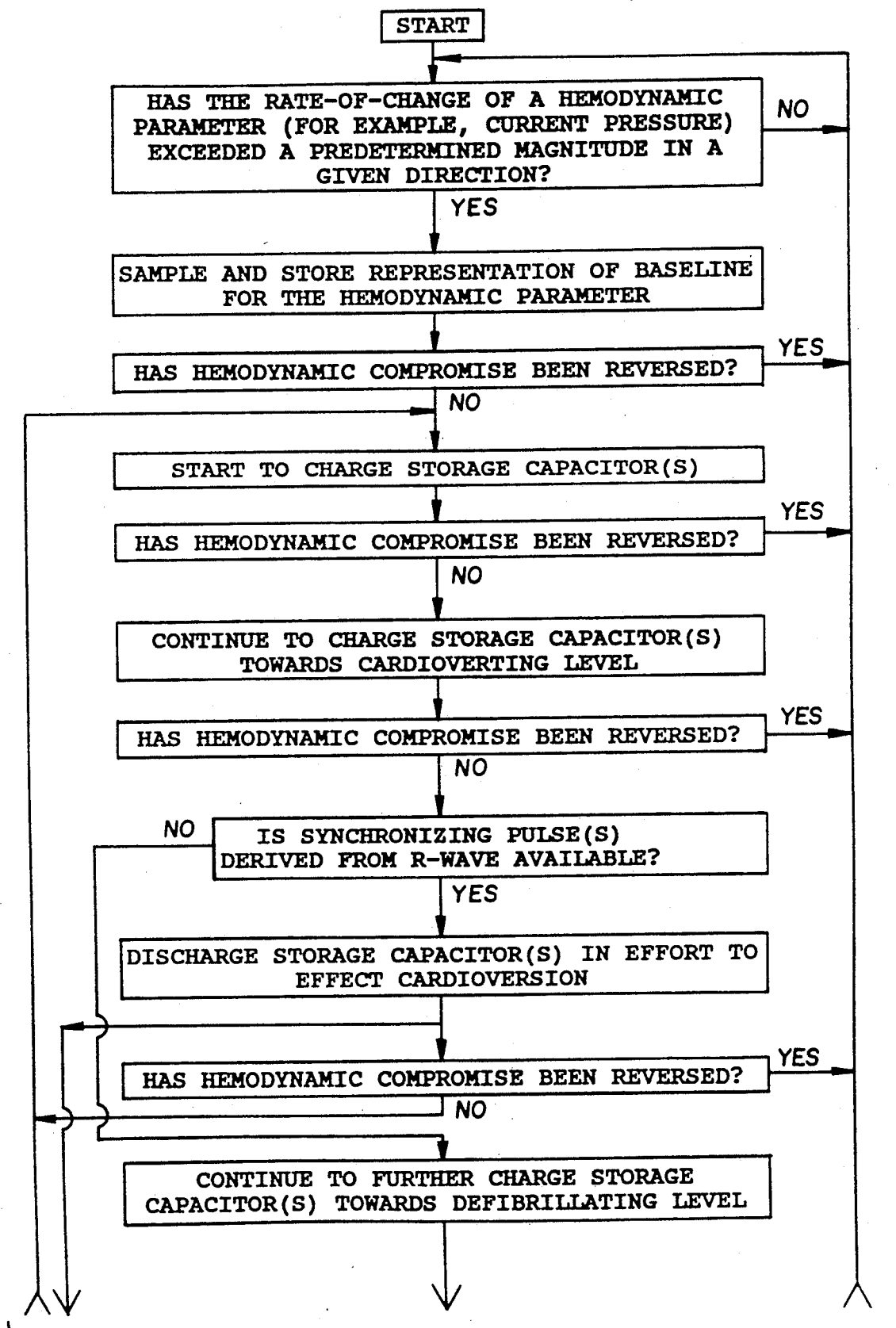
FIGS. 5A and 5B constitute a first exemplary flowchart of a series of actions or steps which may be carried out by the system illustrated in FIG. 4 and effect achievement of a corresponding method.
Figure 5B:
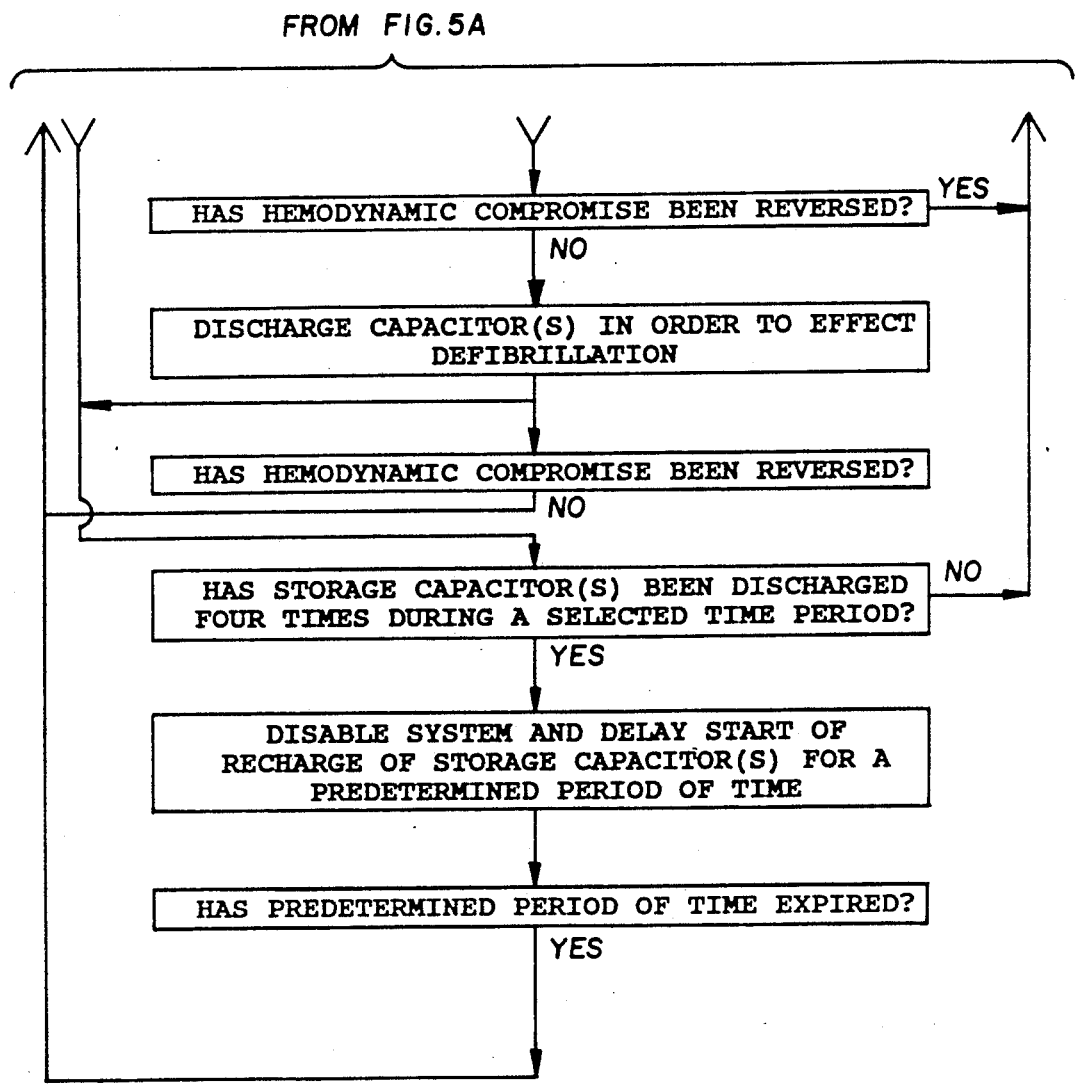

It is to be appreciated that the circuit of FIG. 4 described above may be considered, at least in part, to be a controller or processor, which could be realized as a microprocessor, the processor being identified by the numeral 82. The processor 82, with its associated components, in effect carries out the steps set out in the flowchart of FIGS. 5A and 5B.

The circuit of FIG. 4 could be associated with an antitachycardia pacemaker and/or an antibradycardia pacemaker if desired.

Figure 6:
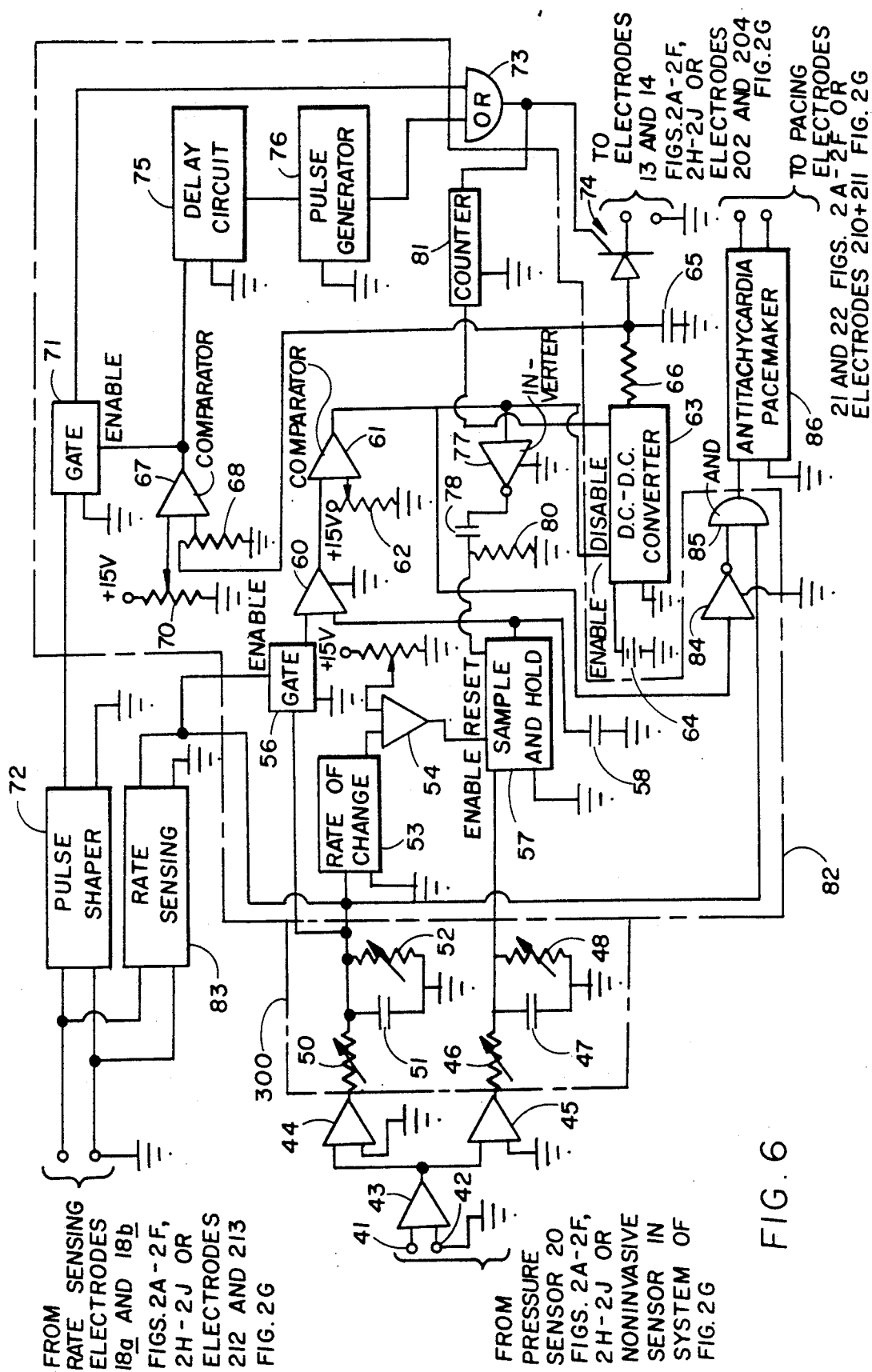
FIG. 6 is a partially block, schematic diagram of a further hemodynamically responsive system for treating a malfunctioning heart which is pressure and rate responsive.

Turning to FIG. 6, a further exemplary embodiment of the circuit components, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 (FIGS. 1, 2A–2F and 2H–2J) or the noninvasive transducer (in system of FIG. 2G) the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 6, with associated components, is suitable for practicing the present invention in which both direction and rate-of-change in current pressure and beating rate criteria are to be taken into account to initiate corrective action. The rate criterion is examined first and, if met, the rate-of-change in pressure criterion is then considered.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage (first signal) across the capacitor 47 represents the mean pressure sensed by the transducer 20 (FIGS. 1, 2A–2F and 2H–2J) or the noninvasive transducer (in system of FIG. 2G) over a relatively long period, for example during the preceding fifteen (15) minutes or even longer (for example a number of hours) or shorter (for example one hundred twenty (120) seconds) being suitable in some cases. The D.C. voltage (first signal) which appears across the capacitor 47, thus represents a long term mean baseline pressure. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components ar such that the D.C. voltage (second signal) which appears across the capacitor 51 represents the short term mean pressure sensed by the transducer 20 (FIGS. 1, 2A–2F and 2H–2J) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to the signal input terminal of a sample-and-hold circuit 57 and to the signal input terminal of a gate 56. The output which appears across the capacitor 51 is also fed to the rate-of-change determining circuit 53. The output from the rate-of-change circuit 53 is directly proportional to the rate-of-change in a given direction of the current pressure. The D.C. output from the rate-of-change determining circuit 53 is fed to a first input terminal of a first comparator 54. The second input to the comparator 54 is connected to the wiper of a potentiometer 55 which is connected between ground and a point of D.C. potential (+15 v). Whenever the voltage supplied to the comparator 54 from the rate-of-change determining circuit 53 exceeds the voltage supplied via the wiper from the potentiometer 55, a low (ZERO) level output on the output terminal from the comparator 54 goes high (ONE). The ONE signal from the comparator is supplied to a sample-and-hold circuit 57 which receives, at its signal input terminal, a voltage representing current mean pressure. When the enable signal appears, the voltage across the capacitor 47 is transferred and stored in a storage circuit, illustrated as a capacitor 58. A rate sensing circuit 83 is arranged to receive a beating rate (R-wave) signal from the rate sensing electrodes 18a, 18b (FIGS. 1, 2A-2F and 2H-2J) or from the rate sensing electrodes 212, 213 (FIG. 2G). Whenever the rate exceeds a given rate, for example 155 beats per minute, indicating tachycardia, the output terminal of the rate sensing circuit 83 goes from low (ZERO) to high (ONE). The ONE signal (first control signal) is supplied as an enabling input to a gate 56. The D.C. voltage representing current mean pressure appearing across the capacitor 51 is fed via the enabled gate 56 to the noninverting input terminal of an operational amplifier 60. The stored D.C. voltage representing mean baseline pressure is supplied to the inverting input terminal of the operational amplifier 60 which has its noninverting input terminal connected to the output terminal of the gate 56 which, when enabled as noted above, passes the D.C. voltage signal appearing across the capacitor 51 and representing current mean pressure to the operational amplifier 60. As illustrated, the input terminals of the operational amplifier are connected as they would be to receive signals representative of a sensed or determined hemodynamic parameter expected to increase during hemodynamic compromise. Were the sensed or determined hemodynamic parameter expected to decrease, the terminals would be reversed.

The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of continuing hemodynamic compromise, the output terminal of the comparator 61 goes from low (ZERO) to high (ONE) and the signal (second control signal) is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse for cardioversion is a truncated exponential pulse of about 25 Joules delivered approximately 17 seconds from onset of the hemodynamic compromise.

Once the capacitor 65 is charged to a sufficiently high D.C. voltage level to provide sufficient energy to effect cardioversion, as determined by a comparator 67, which receives on one input terminal a voltage proportional to the instant D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or from the rate sensing electrodes 212, 213 (FIG. 2G) and produces a pulse train in synchronism with the R-wave supplied from the electrodes 18a, 18b or from the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A-2F and 2H-2J) or the electrodes 202, 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce output pulse to initiate defibrillation. The pulse is supplied, via the OR circuit 73, to the gate electrode of the SCR 74 causing the SCR to fire. The energy storage capacitor 65, which during the elapsed three seconds has charged to a higher level, discharges, via the SCR 74 and the electrodes 13 and 14 (FIGS. 1, 2A-2F and 2H-2J) or electrodes 202 and 204 (FIG. 2G), into the malfunctioning heart via the electrodes 13 and 14 (FIGS. 1, 2A-2F and 2H-2J) or electrodes 202 and 204 (FIG. 2G) in an effort to effect defibrillation, the energy level being higher than it would had been had discharge been effected three (3) or more seconds earlier. The delay circuit may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean pressure and current mean pressure returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure by overcoming the hemodynamic compromise (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to ZERO count whenever it either reaches its maximum count of four or fails to reach the count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 6, cardioverting/defibrillating D.C. pulses are delivered to the malfunctioning heart only when the rate criterion is first satisfied and, thereafter, the pressure criteria also satisfied. This can be viewed as a series rate-of-change in pressure and rate algorithm.

In the event the rate criterion is met, but the rate-of-change in pressure criterion is not; that is to say no hemodynamic compromise presents, the circuit of FIG. 6 nevertheless acts to enable an antitachycardia pacemaker 86 which supplies pacing signals to the pair of pacing electrodes 21, 22 (FIGS. 1, 2A–2F and 2H–2J) or the pair of pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs to the AND circuit 85 are ONE, the antitachycardia pacemaker 86, which may be any one of a number of conventional types is energized.

Figure 7A:
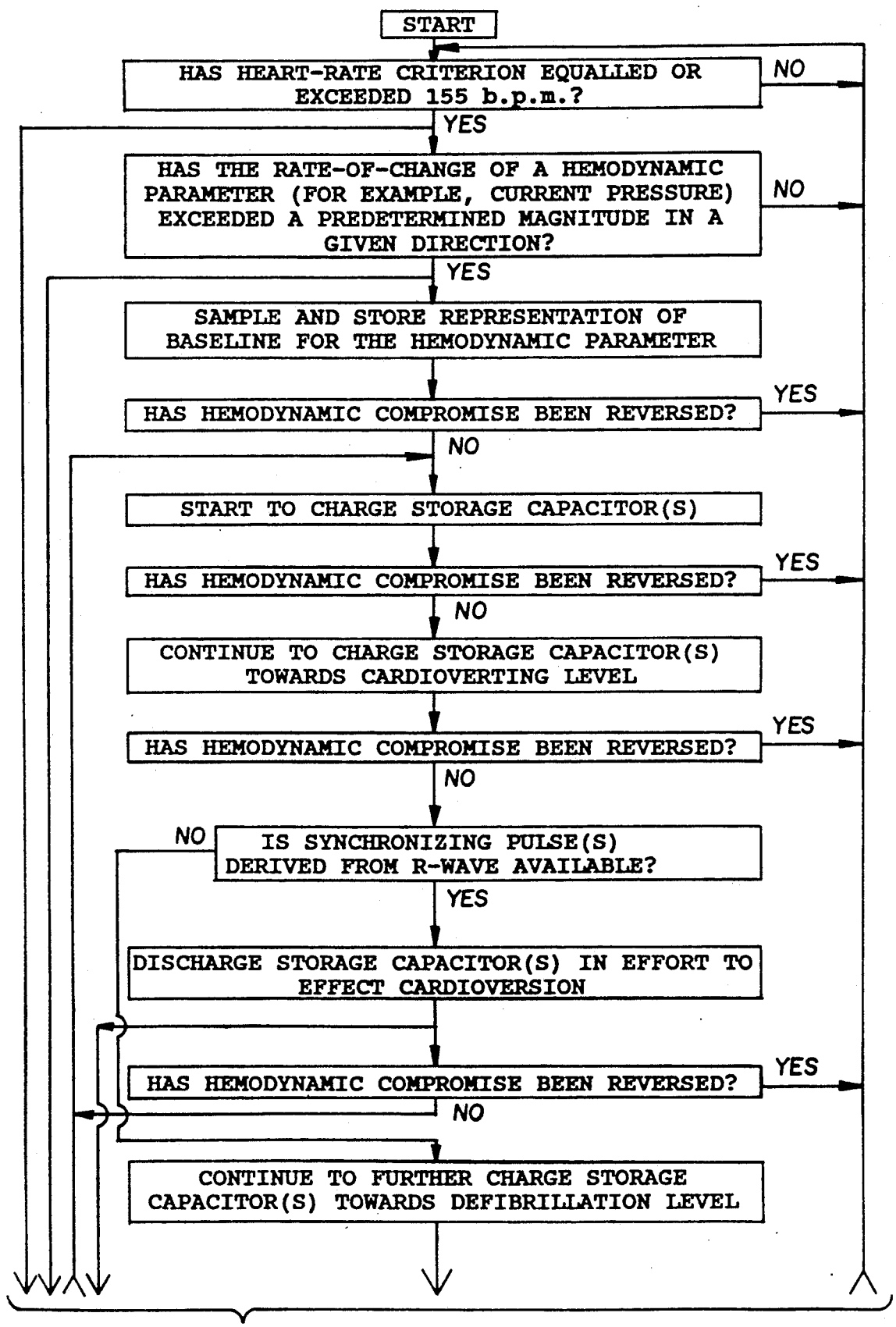
FIGS. 7A and 7B constitute a second exemplary flowchart of a series of actions or steps which may be carried out by the system illustrated in FIG. 6 and effect achievement of a corresponding method.
Figure 7B:
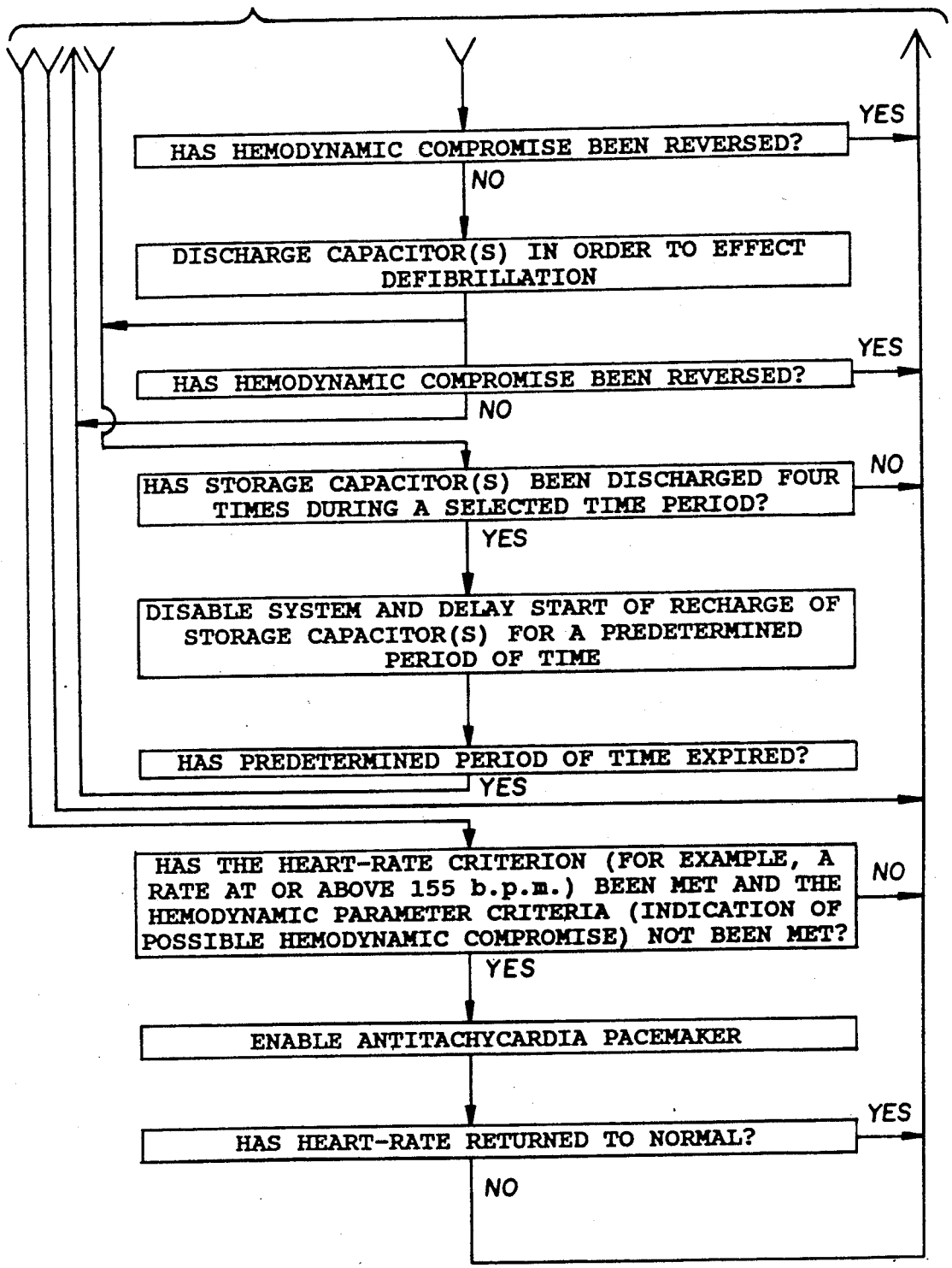

It is to be appreciated that the circuit of FIG. 6 described above may be considered, at least in part, to be a processor, which could be realized as a microprocessor, the processor being identified by the numeral 82. The processor 82, with its associated components, in effect carries out the steps set out in the flowchart of FIGS. 7A and 7B.

It is to be understood that the system of FIG. 6 could be associated with a failsafe antibradycardia pacing system, if desired.

Figure 8:
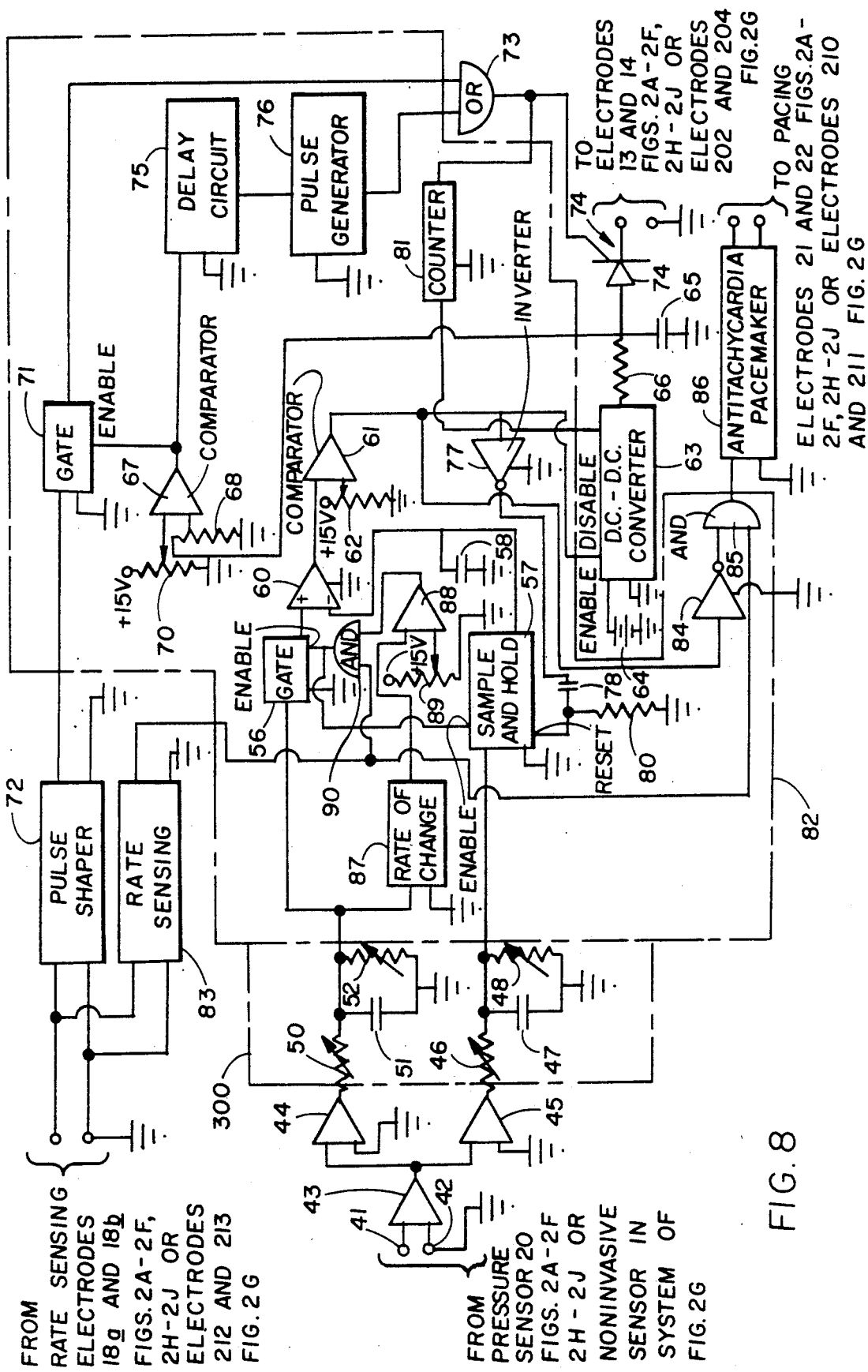
FIG. 8 is a partially block, schematic diagram of hemodynamically responsive system for treating a malfunctioning heart which is a variant of the circuit of FIG. 6.

Turning to FIG. 8, an additional exemplary embodiment of the circuit components, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 (FIGS. 1, 2A–2F and 2H–2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 8 can be used in practicing the present invention using both rate and rate-of-change in pressure criteria. In this case the rate and rate-of-change pressure criteria must exist simultaneously to start the sample-and-hold function.

The output from the buffer amplifier 45 is supplied to an RC circuit constituted by an adjustable resistor 46 connected to ground via a series connected capacitor 47 having a large adjustable resistor 48 connected in parallel therewith. The time constants (charging and discharging) of these circuit components are such that the D.C. voltage across the capacitor 47 represents the mean pressure sensed by the transducer 20 (FIGS. 1, 2A–2F and 2H–2J) or the noninvasive transducer (in system of FIG. 2G) over a relatively long period, for example during the preceding fifteen (15) minutes or even longer for example a number of hours) or shorter (for example one hundred twenty (120) seconds being suitable in some cases. The D.C. voltage (first signal) which appears across the capacitor 47 thus represents a long term mean baseline pressure. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 (FIGS. 1, 2A–2F and 2H–2J) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to a sample-and-hold circuit 57 and to a rate-of-change determining circuit 87, a D.C. voltage signal appearing as the output from the determining circuit 87 is directly proportional to the rate-of-change in pressure of a given algebraic sign. In the case of the preferred pressure parameters MAP, RVPP and RVSP, the direction (slope) would be negative. The D.C. output signal from the rate-of-change determining circuit 87 is fed to a first input terminal of a comparator 88. The second input terminal of the comparator 88 is connected to the wiper of a potentiometer 89 which is connected between ground and a point of fixed D.C. potential, illustrated as being +15 volts, from an internal power supply bus.

Whenever the voltage supplied to the comparator 88 from the rate-of-change determining circuit 87 exceeds the voltage supplied via the wiper from the potentiometer 89, a low (ZERO) level on the output terminal from the comparator 88 goes high (ONE), the ONE signal being coupled to a first input terminal of an AND circuit 90 which has its other input terminal coupled to the output terminal of a rate sensing circuit 83, which produces a ONE signal on its output terminal whenever the heart rate exceeds a predetermined value, for example 155 beats per minute. When the AND gate 90 receives ONE signals on both its input terminals, its output goes high (ONE) which enables a gate 56. The ONE signal from the AND gate 90 is also fed as an enabling input to a sample-and-hold circuit 57. The voltage representing current mean pressure appearing across the capacitor 51 is fed to the noninverting input terminal of an operational amplifier 60. The voltage representing mean baseline pressure appearing across the capacitor 47 is fed to the sample-and-hold circuit 57. Were the selected hemodynamic parameter expected to decrease, the input terminals of the operational amplifier 87 would be reversed.

A D.C. output from the sample-and-hold circuit 57 is stored in a storage circuit, for the purpose of illustration shown as a capacitor 58. This stored voltage is supplied to the inverting input terminal of the operational amplifier 60 which has its noninverting input terminal connected to the output terminal of the gate 56, which when enabled, passes the D.C. voltage signal appearing across the capacitor 51 and representing current mean pressure to the operational amplifier 60. The output from the operational amplifier 60 is supplied to an input terminal of a comparator 61, which has its other input connected to the wiper of a potentiometer 62 connected between ground and the +15 volt power supply bus. As in the species illustrated in FIGS. 4 and 6, the input terminals of the amplifier could be reversed were the pressure at the site monitored to decrease during hemodynamic compromise. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. It is to be appreciated that the wipers of the potentiometers 89 and 62 can be adjusted independently. Thus, one can set the wiper of the potentiometer 62 so that the hemodynamic compromise must get worse than it was when the sample-and-hold circuit 57 is enabled before the output from the comparator 61 enables the D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting-/defibrillation pulses. The desired pulse for effecting cardioversion is a truncated exponential pulse of about 25 Joules delivered approximately 17 seconds from onset of the hemodynamic compromise.

Once the capacitor 65 is charged to a sufficiently high D.C. voltage level, as determined by a comparator 67, which receives on one input terminal a voltage proportional to the D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or the rate sensing electrodes 212, 213 (FIG. 2G) and produces a pulse train in synchronism with the R-wave supplied from the electrodes 18a, 18b or the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A-2F and 2H-2J) or the electrodes 202 and 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse which is supplied, via the OR circuit 73, to the gate electrode of the SCR 74 causing the SCR to fire. The energy storage capacitor 65, which by then has been charged to a higher level, discharges, via the SCR 74 and the electrodes 13 and 14 (FIGS. 1, 2A-2F and 2H-2J) or the electrodes 202 and 204 (FIG. 2G), into the malfunctioning heart in an effort to effect defibrillation. The delay circuit 75 may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean pressure and current mean pressure returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure (which would cause the output of the comparator 61 to become ZERO, removing the enable signal from the converter 63), the capacitor 65 is recharged and discharged a number of additional times, for example three more times, in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to zero whenever either it reaches its maximum count of four or it fails to reach a count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 8, cardioverting/defibrillating D.C. pulses are delivered to the malfunctioning heart only when the rate and the rate-of-change pressure criteria are simultaneously satisfied. This can be viewed as a parallel rate-of-change in pressure algorithm.

In the event the rate criterion is met, but the rate-of-change in pressure criterion is not; that is to say no hemodynamic compromise presents, the circuit of FIG. 8 nevertheless acts to enable an antitachycardia pacemaker 86 which supplies pacing signals to the pair of pacing electrodes 21, 22 (FIGS. 1, 2A-2F and 2H-2J) or the pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs are ONE, the antitachycardia pacemaker 86 is energized.

Figure 9A:
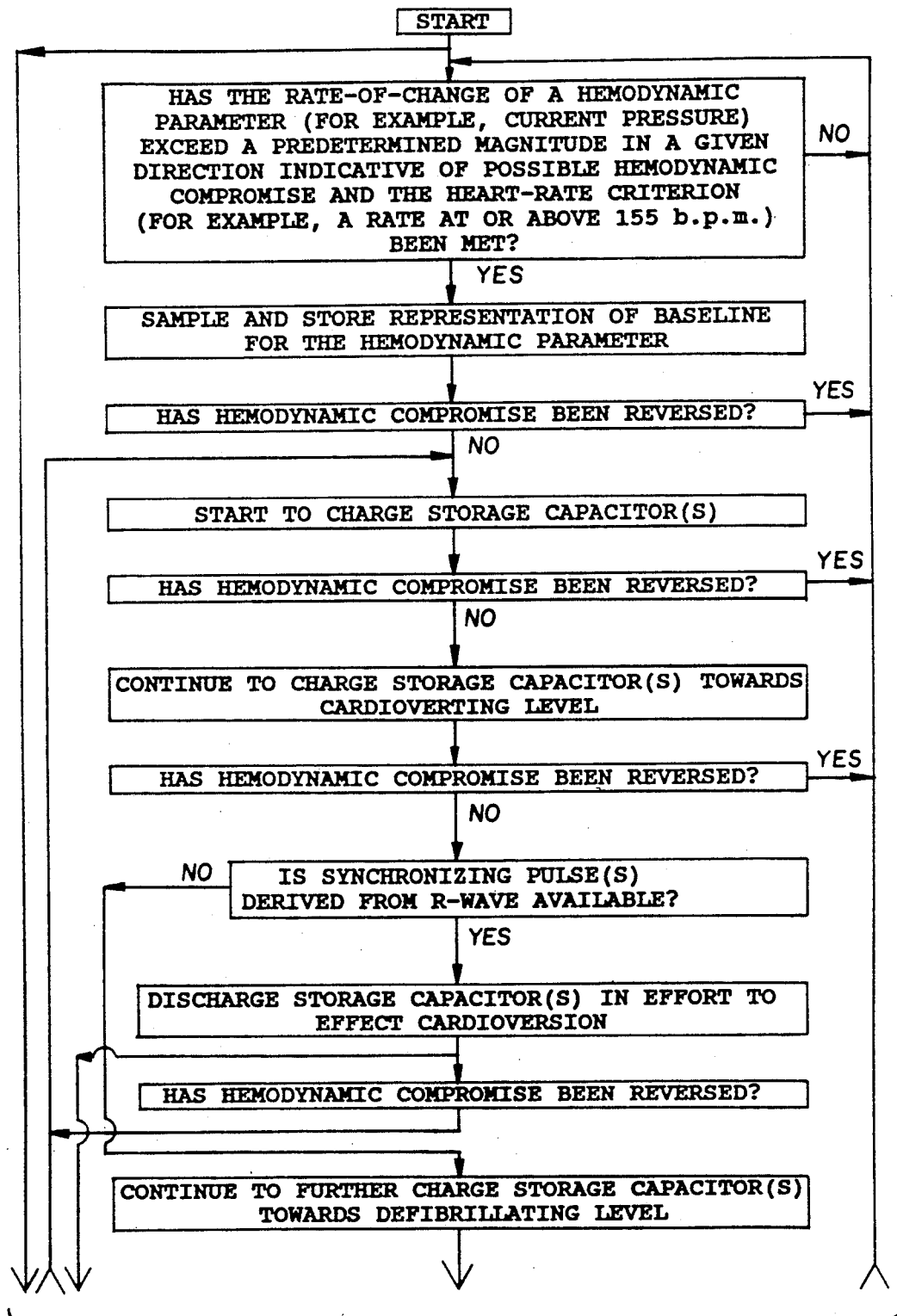
FIGS. 9A and 9B constitute a third exemplary flowchart of a series of actions or steps which may be carried out by the system illustrated in FIG. 8 and effect achievement of a corresponding method.
Figure 9B:
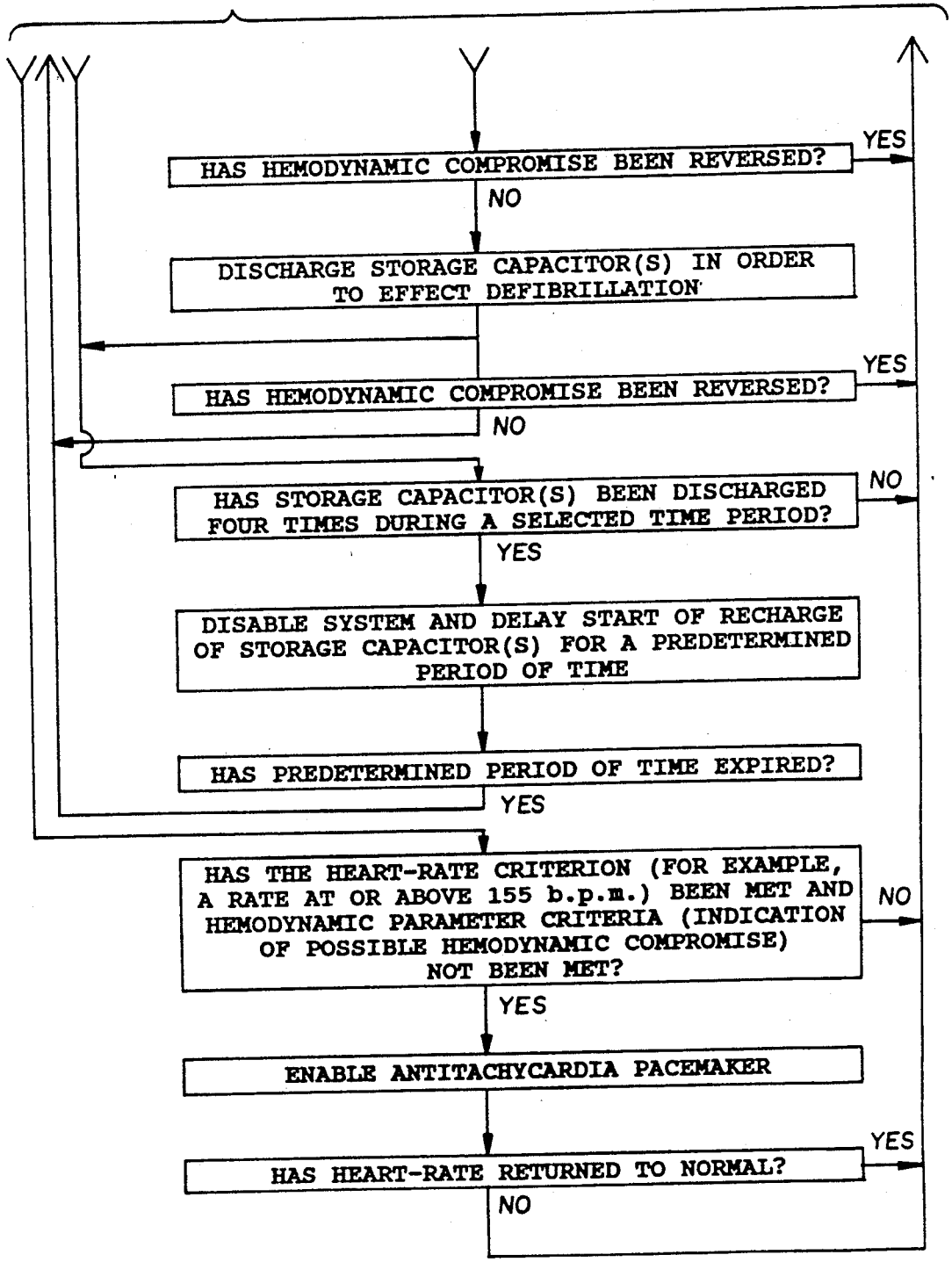

It is to be appreciated that the circuit described above may be considered, at least in part, to be a controller processor, which could be realized as a microprocessor, the processor being identified by the numeral 82. The processor 82, with its associated components, in effect carries out the steps set out in the flowchart of FIGS. 9A and 9B.

The circuit of FIG. 8 could be associated with a failsafe antibradycardia pacemaker, if desired.

Figure 15:
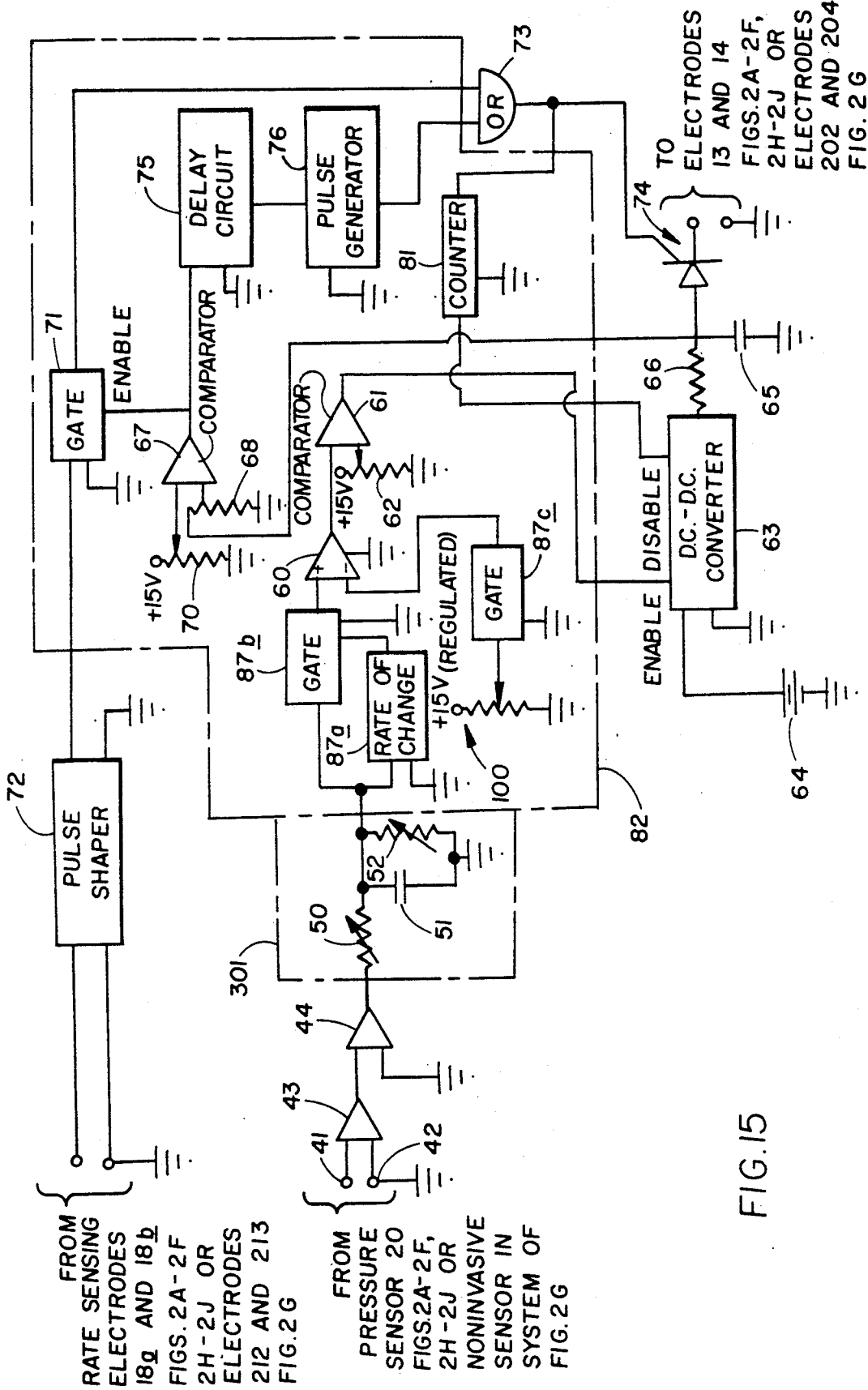
FIG. 15 is a partially block, schematic diagram of a hemodynamically responsive system for treating a malfunctioning heart in accordance with an exemplary embodiment of the invention which is pressure responsive.

Turning to FIG. 15, an exemplary embodiment of circuit components of the present invention, which may be positioned within the housing 12 (FIGS. 1 and 3) or the bed-side apparatus 208 (FIG. 2G), includes a pair of input terminals 41, 42 which receive the variable D.C. voltage output signal representing pressure from the pressure responsive transducer 20 (FIGS. 1, 2A-2F and 2H-2J) or noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to a buffer amplifier 44. The circuit of FIG. 15 is suitable for practicing the present invention using a pressure-only criteria.

A D.C. voltage level (first signal) representative of fixed baseline pressure appears on the wiper of a potentiometer 100 which may be set by a medical professional to suit the particular patient involved. The potentiometer 100 is connected, as illustrated, between system ground and a point of +15 volts, regulated. The medical professional, based on a patient's condition and history, could set the wiper of the potentiometer at a suitable patient-specific point, reflecting an appropriate baseline. It is to be understood that the point may be selected prior to implantation. The circuit may be adapted to enable the patient-specific set point to be changed, the set using radio and/or magnetic coupling (not shown).

The term "mean" as used herein is broad and includes the average value as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean pressure sensed by the transducer 20 (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds). The resistors 50 and 52 may be set by a medical professional to suit the particular patient involved, so far as what the most suitable period length (period of given length) for current data acquisition appears to be most suitable. Were the device already implanted, conventional radio or magnetic links could be used to change the setting of the variable resistors 50 and 51 were a patient's condition to make such adjustments desirable.

As illustrated the baseline and short term (current) D.C. voltage signals which appear respectively on the wiper of the potentiometer 100 and across the capacitor 51 are fed respectively to a rate-of-change determining circuit 87a and to a gate 87c. Whenever the rate-of-change determining circuit 87a detects a rate-of-change in pressure of at least a predetermined magnitude in a given direction (of given algebraic sign) it provides an enabling output to the gates 87b and 87c allow the respective passage of the short term pressure related signal, which appears across the capacitor 51, and the baseline signal, which appears on the wiper of the potentiometer 100, to the respective noninverting and inverting terminals of an operational amplifier 60. The rate-of-change determining circuit 87a operates to supply the enabling inputs to the gates 87a and 87b once an unacceptable magnitude in the rate-of-change has been detected so as to enable them for a term long enough to assure the remaining circuitry will respond and effect defibrillation and/or cardioversion. A difference D.C. voltage signal appears as the output from the operational amplifier 60. As shown, the inverting and noninverting terminals of the operational amplifier 60 are connected as they would be were the hemodynamic parameter expected to increase during hemodynamic compromise. Were the hemodynamic parameter involved expected to decrease, the terminals would be reversed. The D.C. output signal from the operational amplifier 60 is fed to a first input terminal of a first comparator 61, the second input terminal of the comparator 61 is connected to the wiper of a potentiometer 62 which is connected between ground and a point of fixed D.C. potential, illustrated as being +15 volts, from an internal power supply bus.

Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or a capacitor pack), via a resistor 66 towards the high voltage. The capacitor 65 is of such size that it will store energy levels sufficient to produce the desired cardioverting/defibrillation pulses. The desired pulse may be a truncated exponential pulse of about 25 Joules delivered approximately 17 seconds from onset of the hemodynamic compromise. The pulse could, especially when defibrillation is being undertaken after a failed attempt to cardiovert, be delivered somewhat later and with a higher energy level.

Once the capacitor 65 is charged to a sufficiently high D.C. voltage level to provide sufficient energy to effect cardioversion, as determined by a comparator 67, which receives on one input terminal a voltage proportional to the increasing D.C. voltage across the capacitor 65, a highly resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input terminal connected to receive an output from a pulse shaper 72, which receives an input from the rate sensing electrodes 18a, 18b (FIGS. 1, 2A-2F and 2H-2J) or from the rate sensing electrodes 212, 213 (FIG. 2G) and produces a pulse train in synchronism with the R-wave supplied from the electrodes 18a, 18b or electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy then stored on the capacitor 65 (or the bank of capacitors) into the malfunctioning heart, via the electrodes 13 and 14 (FIGS. 1, 2A-2F and 2H-2J) or the electrodes 202 and 204 (FIG. 2G) in an effort to effect cardioversion, the discharge being in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more and enables a pulse generator 76 causing it to produce an output pulse to initiate defibrillation which is supplied, via the OR circuit 73, to the gate electrode of the SCR 74 causing the SCR to fire. The energy storage capacitor 65 (or the bank of capacitors), which by then has charged to a higher level discharges, via the SCR 74 and the electrodes 13 and 14 (FIGS. 1, 2A-2F and 2H-2J) or the electrodes 202 and 204 (FIG. 2G), into the malfunctioning heart in an effort to effect defibrillation, the energy level being higher than would have been the case had the capacitor been discharged three seconds earlier. The delay circuit may be composed of an RC circuit connected to the comparator 67 so that the capacitor thereof charges toward the ONE level slowly; for example the capacitor may take about three (3) seconds or more as indicated above to achieve the ONE level, allowing time to receive one or more synchronizing pulses from the pulse shaper 72, if present.

In the event the first pulse delivered to the heart fails to effect a correction in the pressure (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. An internal timer within the converter 63 holds the converter OFF for a given period so that the patient will not receive more shocks during this given period. At the end of the period the converter 63 returns to a READY condition and is again able to respond to an ENABLE signal from the comparator 61. The counter 81 resets itself to zero whenever it either reaches its maximum count of four or fails to reach the count of four within the given time period.

In the event cardioversion or defibrillation is successful, the short term mean current pressure (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the pressure condition sensed indicates that hemodynamic compromise is again present. In the event the short term mean current pressure returns to normal before the first cardioverting or defibrillating pulse is delivered, the output of the comparator goes to low (ZERO), removing the enable signal from the converter 63, thus stopping the charging of the capacitor 65.

Figure 16A:
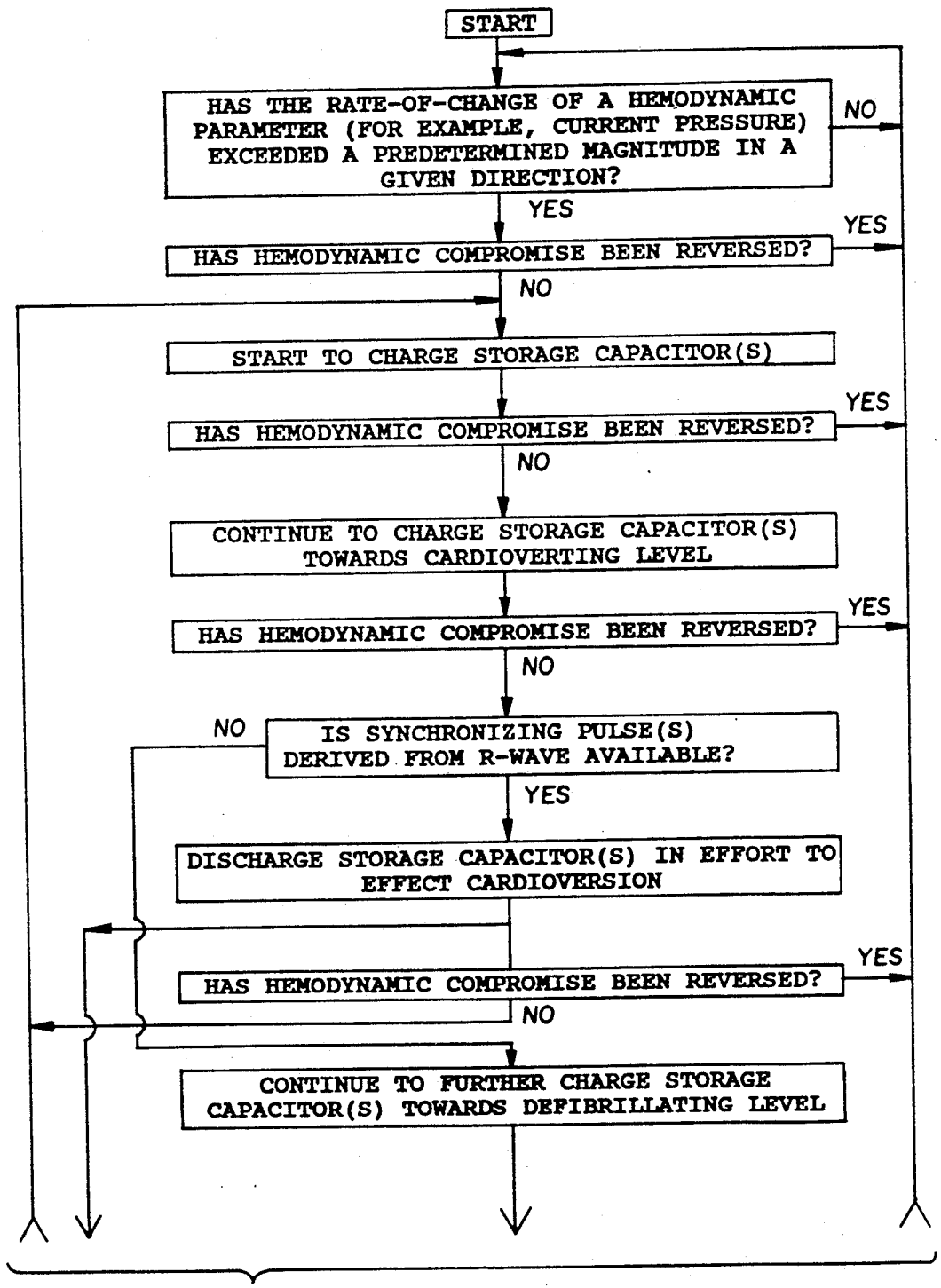
FIGS. 16A and 16B constitute an exemplary flowchart of a series of actions or steps which may be carried out by the system of the present invention illustrated in FIG. 15 and effect achievement of the invention in its method aspect.
Figure 16B:
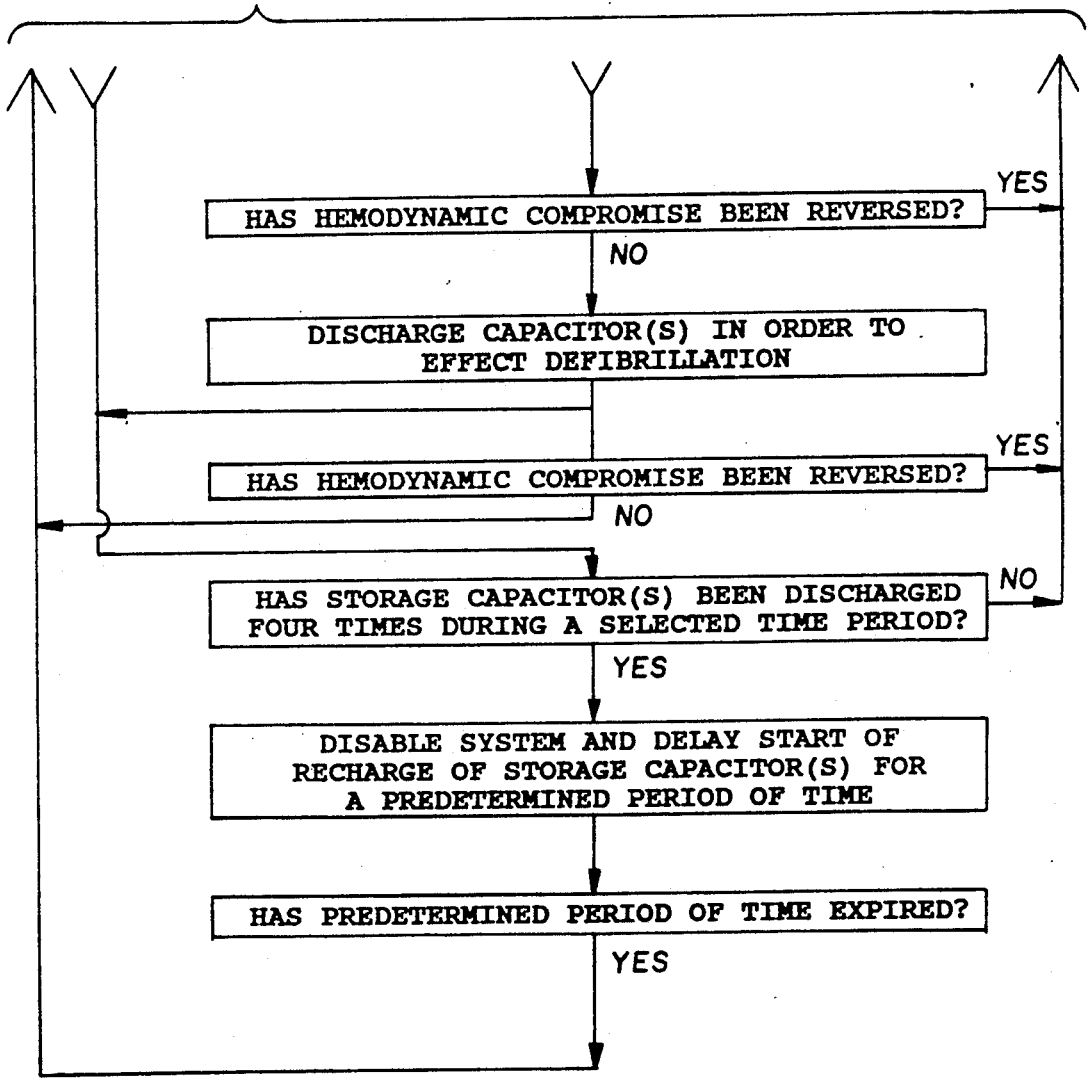

It is to be appreciated that the circuit of FIG. 15 described above may be considered, at least in part, to be a controller or processor, which could be realized as a microprocessor, the processor being identified by the numeral 82. The processor 82, with its associated components, in effect carries out the steps set out in the flowchart of FIGS. 16A and 16B.

The circuit of FIG. 15 could be associated with an antitachycardia pacemaker and/or an antibradycardia pacemaker, if desired.

Figure 17:
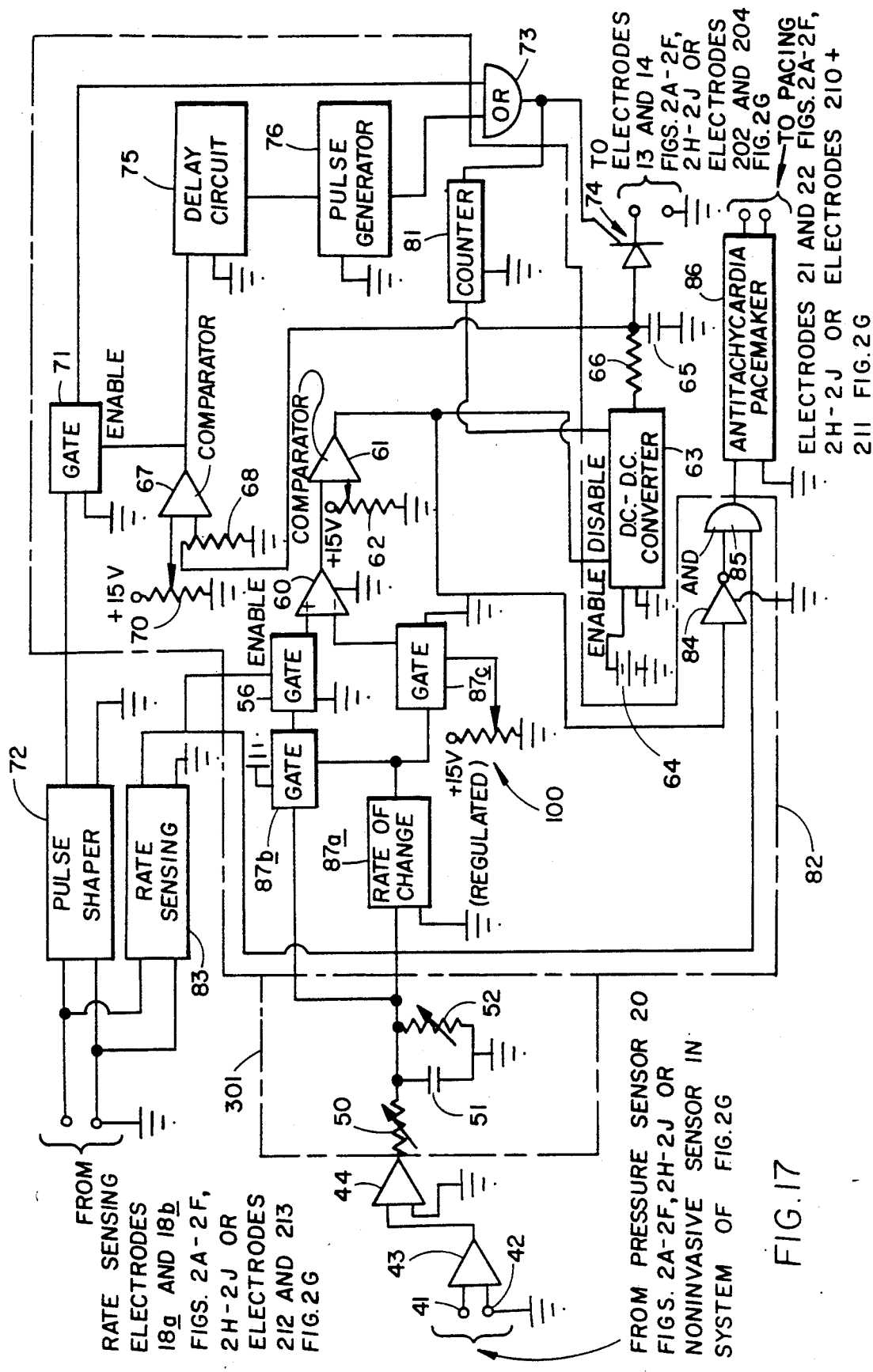
FIG. 17 is a partially block, schematic diagram of a hemodynamically responsive system for treating a malfunctioning heart in accordance with a further exemplary embodiment of the invention which is pressure and rate responsive.

Turning to FIG. 17, a further exemplary embodiment of the circuit components of the present invention, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 (FIGS. 1, 2A-2F and 2H-2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to a buffer amplifier 44. The circuit of FIG. 17, with associated components, is suitable for practicing the present invention in which both rate-of-change of pressure and beating rate criteria are to be taken into account. The rate criterion is examined first and, if met, the rate-of-change of pressure criterion is then considered.

A D.C. voltage level (first signal) provided on the wiper of a potentiometer 100, which is connected between ground and a regulated +15 volts source, represents a fixed baseline pressure. The wiper may be set by a medical professional taking into account the history and condition of the particular patient. The potentiometer 100 may be adjusted, possibly using conventional magnetic or radio links as noted above.

The term "mean" as used herein is broad and includes the average value, as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components ar such that the D.C. voltage (second signal) which appears across the capacitor 51 represents the short term mean pressure sensed by the transducer 20 (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds). As in the circuit of FIG. 15, the resistors 50 and 51 may be adjusted, taking into account the patient's possibly changing condition, possibly using conventional radio or magnetic links.

As illustrated the baseline and short term (current) D.C. voltage signals appear respective on the wiper of the potentiometer 100 and across the capacitor 51. The voltage (second signal) from the capacitor 51 is fed to the signal input terminal of a gate 56, via a gate 87b. The gate 87b is enabled by output from a rate-of-change determining circuit 87a which provides an enabling output to a gate 87b, as well as a gate 87c upon the rate-of-change in the pressure (as reflected by the changing signal across the capacitor 51) having a magnitude and algebraic sign indicative of possible hemodynamic compromise. The rate-of-change determining circuit, once the acceptable rate-of-change and algebraic sign thereof have been determined to have occurred, provides an enable signal for a term of sufficient to allow the other circuit components to attempt cardioversion and/or defibrillation. A rate sensing circuit 83 is arranged to receive a beating rate (R-wave) signal from the rate sensing electrodes 18a, 18b (FIGS. 1, 2A-2F and 2H-2J) or from the rate sensing electrodes 212, 213 (FIG. 2G). Whenever the rate exceeds a given rate, for example 155 beats per minute, indicating tachycardia, the output terminal of the rate sensing circuit 83 goes from low (ZERO) to high (ONE). The ONE signal (first control signal) is supplied as an enabling input to the gate 56. The D.C. voltage representing current mean pressure appearing across the capacitor 51 is fed via the enabled gate 87b and the enabled gate 56 to the noninverting input terminal of an operational amplifier 60. The D.C. voltage (first signal) representing baseline pressure appearing on the wiper of the potentiometer 10 is supplied, via the enabled gate 87c to the inverting input terminal of the operational amplifier 60 which has its noninverting input terminal connected to the output terminal of the gate 56 which, when enabled as noted above, passes the D.C. voltage signal appearing across the capacitor 51 and representing current mean pressure to the operational amplifier 60. As illustrated, the input terminals of the operational amplifier 60 are connected as they would be to receive signals representative of sensed or determined parameters which are expected to increase during hemodynamic compromise. Were the selected hemodynamic parameter expected to drop during hemodynamic compromise, the terminals would be reversed.

The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) and the signal (second control signal) is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or a pack of capacitors), via a resistor 66 towards the high voltage. The capacitor 65 is of such size that it will store energy levels sufficient to produce the desired cardioverting/defibrillation pulses. The desired pulse for cardioversion may be a truncated exponential pulse of about 25 Joules delivered approximately 17 seconds from onset of the hemodynamic compromise.

Once the capacitor 65 is charged to a sufficiently high D.C. voltage level to provide sufficient energy to effect cardioversion, as determined by a comparator 67, which receives on one input terminal a voltage proportional to the instant D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A-2F and 2H-2J) or from the rate sensing electrodes 212, 213 (FIG. 2G) and produces a pulse train in synchronism with the R-wave supplied from the electrodes 18a, 18b or from the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A-2F and 2H-2J) or the electrodes 202, 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse to initiate defibrillation. The pulse is supplied, via the OR circuit 73, to the gate electrode of the SCR 74 causing the SCR to fire. The energy storage capacitor 65 (or a pack of capacitors), which during the elapsed three seconds has charged to a higher level, discharges, via the SCR 74 and the electrodes 13 and 14 (FIGS. 1, 2A-2F and 2H-2J) or electrodes 202 and 204 (FIG. 2G), into the malfunctioning heart via the electrodes 13 and 14 (FIGS. 1, 2A-2F and 2H-2J) or electrodes 202 and 204 (FIG. 2G) in an effort to effect defibrillation, the energy level being higher than it would had been had discharge been effected three (3) or more seconds earlier. The delay circuit may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

In the event the first pulse delivered to the heart fails to effect a correction in the pressure by overcoming the hemodynamic compromise (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to ZERO count whenever it either reaches its maximum count of four or fails to reach the count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 17, cardioverting/defibrillating D.C. pulses are delivered to the malfunctioning heart only when the rate criterion is first satisfied and, thereafter, the pressure criteria also satisfied. This can be viewed as a series rate-pressure algorithm.

In the event the rate criterion is met, but the rate-of-change in pressure criterion is not; that is to say no hemodynamic compromise presents, the circuit of FIG. 17 nevertheless acts to enable an antitachycardia pacemaker 86 which supplies pacing signals to the pair of pacing electrodes 21, 22 (FIGS. 1, 2A-2F and 2H-2J) or the pair of pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs to the AND circuit 85 are ONE, the antitachycardia pacemaker 86, which may be any one of a number of conventional types is energized.

In the event cardioversion or defibrillation is successful, the short term mean current pressure (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the pressure condition sensed indicates that hemodynamic compromise is again present. In the event the short term current pressure returns to normal before any cardioverting or defibrillating pulses are delivered (as in the case of FIG. 15), the enable signal is revived from the converter 63 and the charging of the capacitor 65 stops.

Figure 18A:
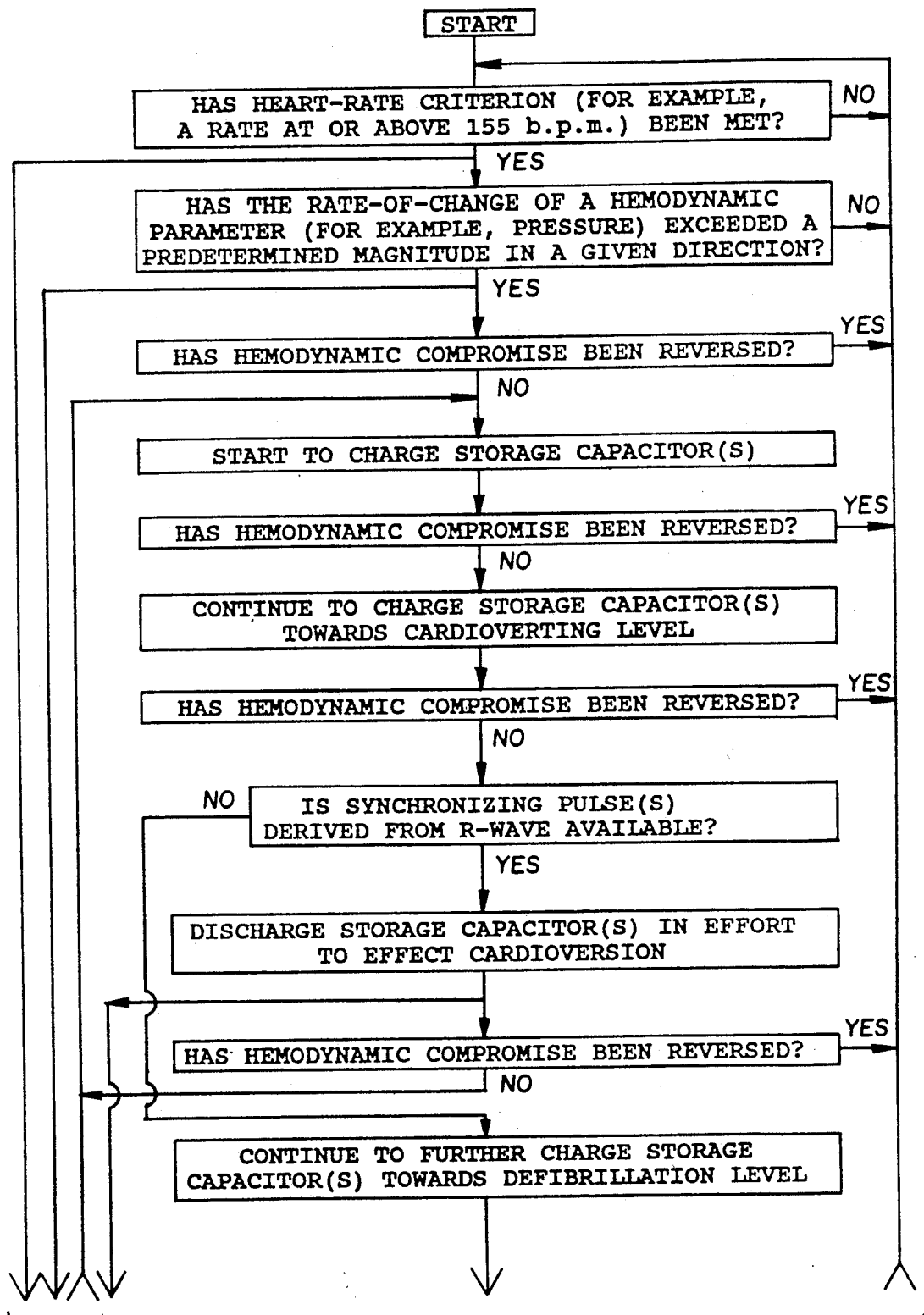
FIGS. 18A and 18B constitute a further exemplary flowchart of a series of actions or steps which may be carried out by the system of the present invention illustrated in FIG. 17 and effect achievement of the invention in its method aspect.
Figure 18B:
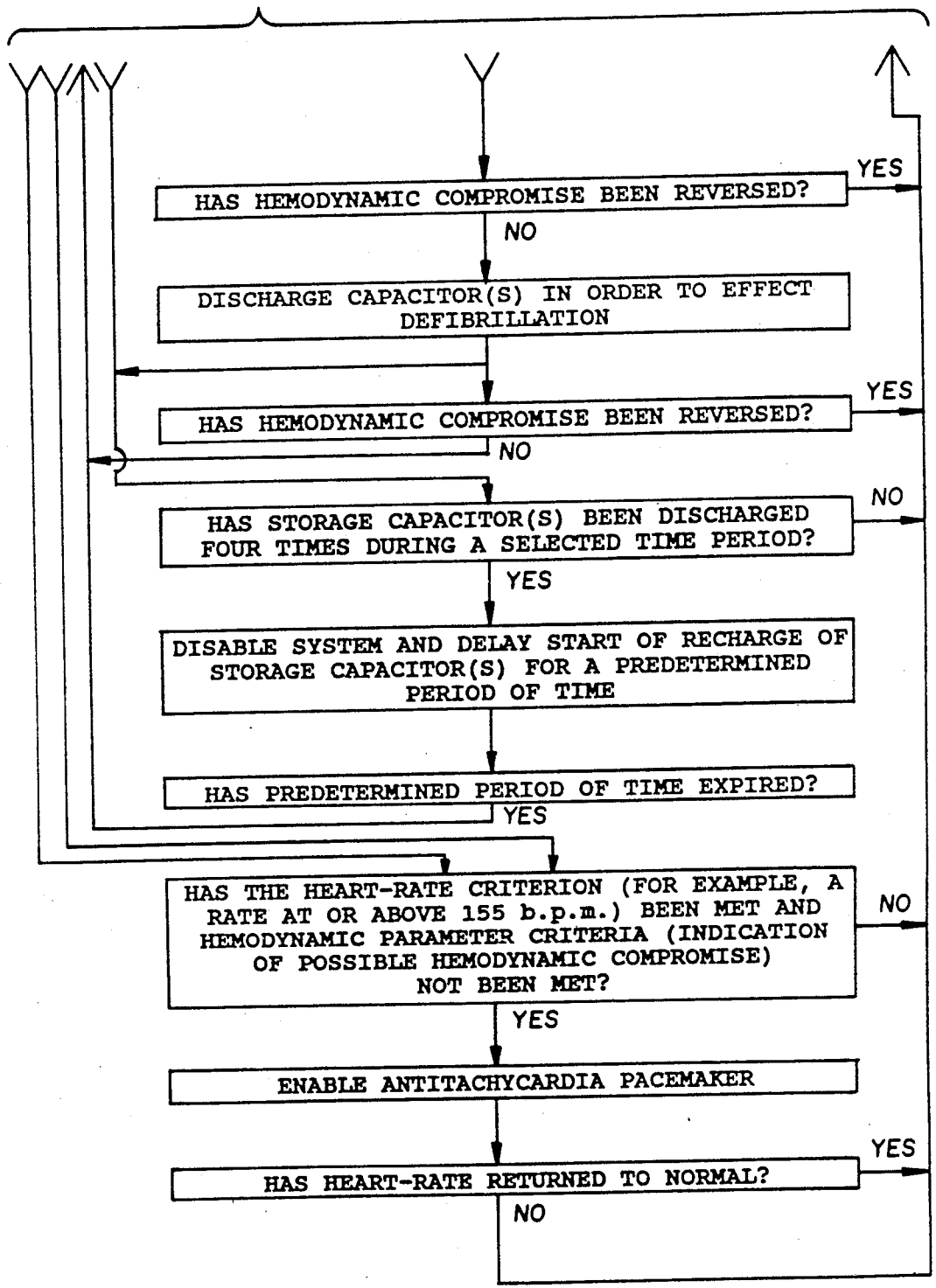

It is to be appreciated that the circuit of FIG. 17 described above may be considered, at least in part, to be a processor, which could be realized as a microprocessor, the processor being identified by the numeral 82. The processor 82, with its associated components, in effect carries out the steps set out in the flowchart of FIGS. 18A and 18B.

It is to be understood that the system of FIG. 17 could be associated with a failsafe antibradycardia pacing system, if desired.

Figure 19:
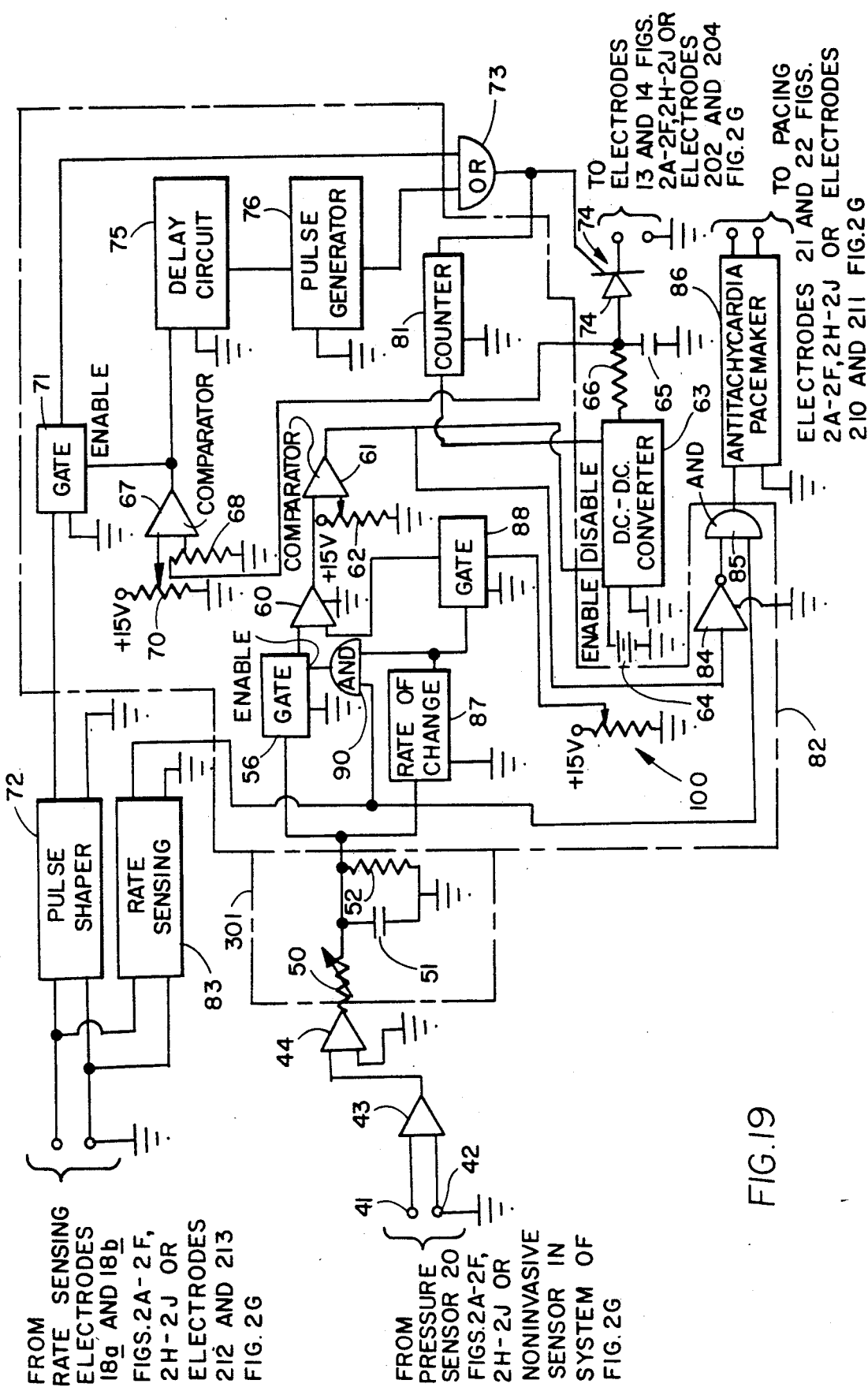
FIG. 19 is a partially block, schematic diagram of hemodynamically responsive system for treating a malfunctioning heart which is a variant of the circuit of FIG. 17.

Turning to FIG. 19, another exemplary embodiment of the circuit components of the present invention, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 (FIGS. 1, 2A-2F and 2H-2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to buffer amplifier 44. The circuit of FIG. 19 can be used in practicing the present invention using both heart rate and rate-of-change in pressure criteria. In this case the heart rate and rate-of-change in pressure criteria must exist simultaneously to enable the system.

A D.C. voltage level (first signal) appears on the wiper of a potentiometer 100, which is connected between ground and a regulated +15 volt source, the signal representing fixed baseline pressure. The wiper (as in the circuits of FIGS. 15 and 17) may be set by a medical professional in accordance with needs of a specific patient and may be adjusted later, if desired, using radio or magnetic techniques.

The term "mean" as used herein is broad and includes the average value, as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage which appears across the capacitor 51 represents the short term mean pressure sensed by the transducer 20 (FIGS. 1, 2A-2F and 2H-2J) or the noninvasive transducer (in system of FIG. 2G) over a relatively short period, for example, during the preceding fifteen (15) seconds or longer (for example 60 seconds) or shorter (for example six seconds). The size of the resistors 50 and 51 (as in the circuits of FIGS. 15 and 17) may be adjusted, a desirable feature were a patient's condition or needs to change.

As illustrated the baseline and short term (current) D.C. voltage signals which respectively appear on the wiper 100 of the potentiometer 100 and across the capacitor 51 are fed respectively to the inverting and noninverting terminals of an operational amplifier 60 via respective gates 88 and 56, a difference D.C. voltage signal appearing as the output from the amplifier 60. As illustrated, the input terminals of the operational amplifier 60 are connected as they would be were the hemodynamic parameter sensed or determined expected to increase during hemodynamic compromise. Were the sensed or determined selected hemodynamic parameter expected to decrease, the terminals would be reversed. A rate-of-change determining circuit 87 is operatively arranged to receive a signal from the capacitor 51 and produce an output whenever the magnitude and is of given algebraic sign of the rate-of-change of the signal exceeds a predetermined magnitude, indicating possible hemodynamic compromise. The D.C. output signal from the rate-of-change determining circuit 87 is fed to the enable input terminal of the gate 88. The signal input terminal of the gate 88 is connected to the wiper of a potentiometer 89 which is connected between ground and a point of fixed D.C. potential, illustrated as being +15 volts, from an internal power supply bus.

Whenever the D.C. voltage supplied, as an enabling signal, to the gate 88 from the rate-of-change determining circuit 87 is present voltage is supplied from the wiper of the potentiometer 89 to the inverting input terminal of the operational amplifier 60. The enabling output from the rate-of-change determining circuit 87 is also supplied to a first input terminal of an AND circuit 90 which has its other input terminal coupled to the output terminal of a rate sensing circuit 83, which produces a ONE signal on its output terminal whenever the heart rate exceeds a predetermined value, for example 155 beats per minute. When the AND gate 90 receives ONE signals on both its input terminals, its output goes high (ONE) which enables a gate 56. The voltage (second signal) representing current mean pressure appearing across the capacitor 51 is fed to the noninverting input terminal of an operational amplifier 60. The voltage (first signal) representing fixed baseline pressure appearing on the wiper of the potentiometer 100 is fed to the inverting input terminal of the operational amplifier 60, as noted above. Were the selected hemodynamic parameter expect to decrease, the input terminals of the operational amplifier 60 would be reversed. The operational amplifier 60 which has its noninverting input terminal connected to the output terminal of the gate 56, which when enabled, passes the D.C. voltage signal appearing across the capacitor 51 and representing current mean pressure to the operational amplifier 60. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. It is to be appreciated that the wipers of the potentiometers 89 and 62 can be adjusted independently. Thus, one can set the wiper of the potentiometer 62 so that the hemodynamic compromise must get worse than it was when the gate 56 was opened before the output from the comparator 61 enables the D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or capacitor pack), via a resistor 66 towards the high voltage. The capacitor 65 is of such size that it will store energy levels sufficient to produce the desired cardioverting-/defibrillation pulses. The desired pulse for effecting cardioversion may be a truncated exponential pulse of about 25 Joules delivered approximately 17 seconds from onset of the hemodynamic compromise.

Once the capacitor 65 is charged to a sufficiently high D.C. voltage level, as determined by a comparator 67, which receives on one input terminal a voltage proportional to the D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A–2F and 2H–2J) or the rate sensing electrodes 212, 213 (FIG. 2G) and produces a pulse train in synchronism with the R-wave supplied from the electrodes 18a, 18b or the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A–2F and 2H–2J) or the electrodes 202 and 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse which is supplied, via the OR circuit 73, to the gate electrode of the SCR 74 causing the SCR to fire. The energy storage capacitor 65, which by then has been charged to a higher level, discharges, via the SCR 74 and the electrodes 13 and 14 (FIGS. 1, 2A–2F and 2H–2J) or the electrodes 202 and 204 (FIG. 2G), into the malfunctioning heart in an effort to effect defibrillation. The delay circuit 75 may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

In the event the first pulse delivered to the heart fails to effect a correction in the pressure (which would cause the output of the comparator 61 to become ZERO, removing the enable signal from the converter 63), the capacitor 65 is recharged and discharged a number of additional times, for example three more times, in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to zero whenever either it reaches its maximum count of four or it fails to reach a count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 19, cardioverting/defibrillating D.C. pulses are delivered to the malfunctioning heart only when the heart rate and the and rate-of-change in pressure criteria are simultaneously satisfied. This can be viewed as a parallel rate-pressure algorithm.

In the event the heart rate criterion is met, but the rate-of-change in pressure criterion is not; that is, to say no hemodynamic compromise presents, the circuit of FIG. 19 nevertheless acts to enable an antitachycardia pacemaker 86 which supplies pacing signals to the pair of pacing electrodes 21, 22 (FIGS. 1, 2A–2F and 2H–2J) or the pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs are ONE, the antitachycardia pacemaker 86 is energized.

In the event cardioversion or defibrillation is successful, the short term mean current pressure (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the pressure condition sensed indicates that hemodynamic compromise is again present.

Figure 20A:
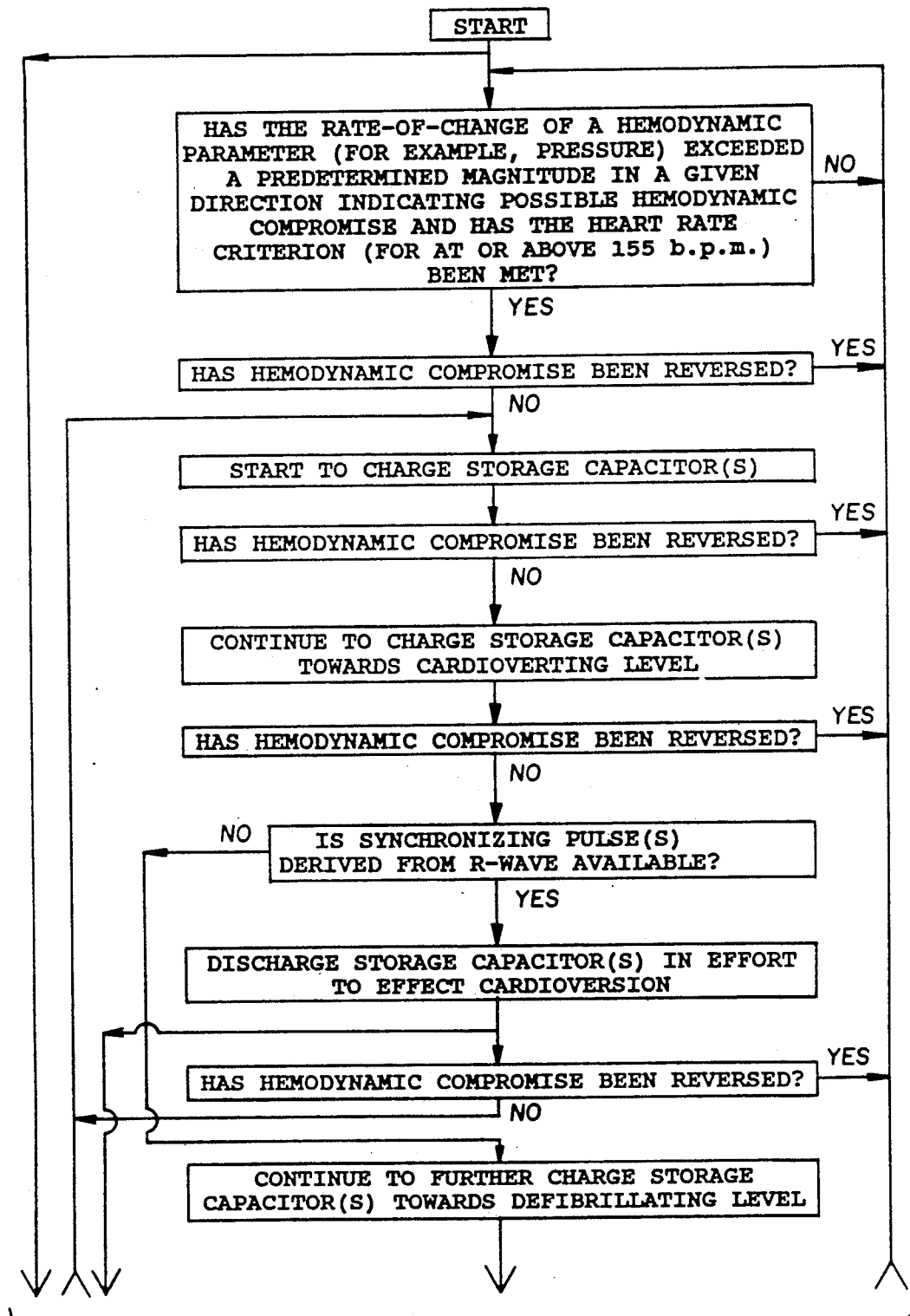
FIGS. 20A and 20B constitute an additional exemplary flowchart of a series of actions or steps which may be carried out by the system of the present invention as illustrated in FIG. 19 and effect achievement of the invention in its method aspect.
Figure 20B:
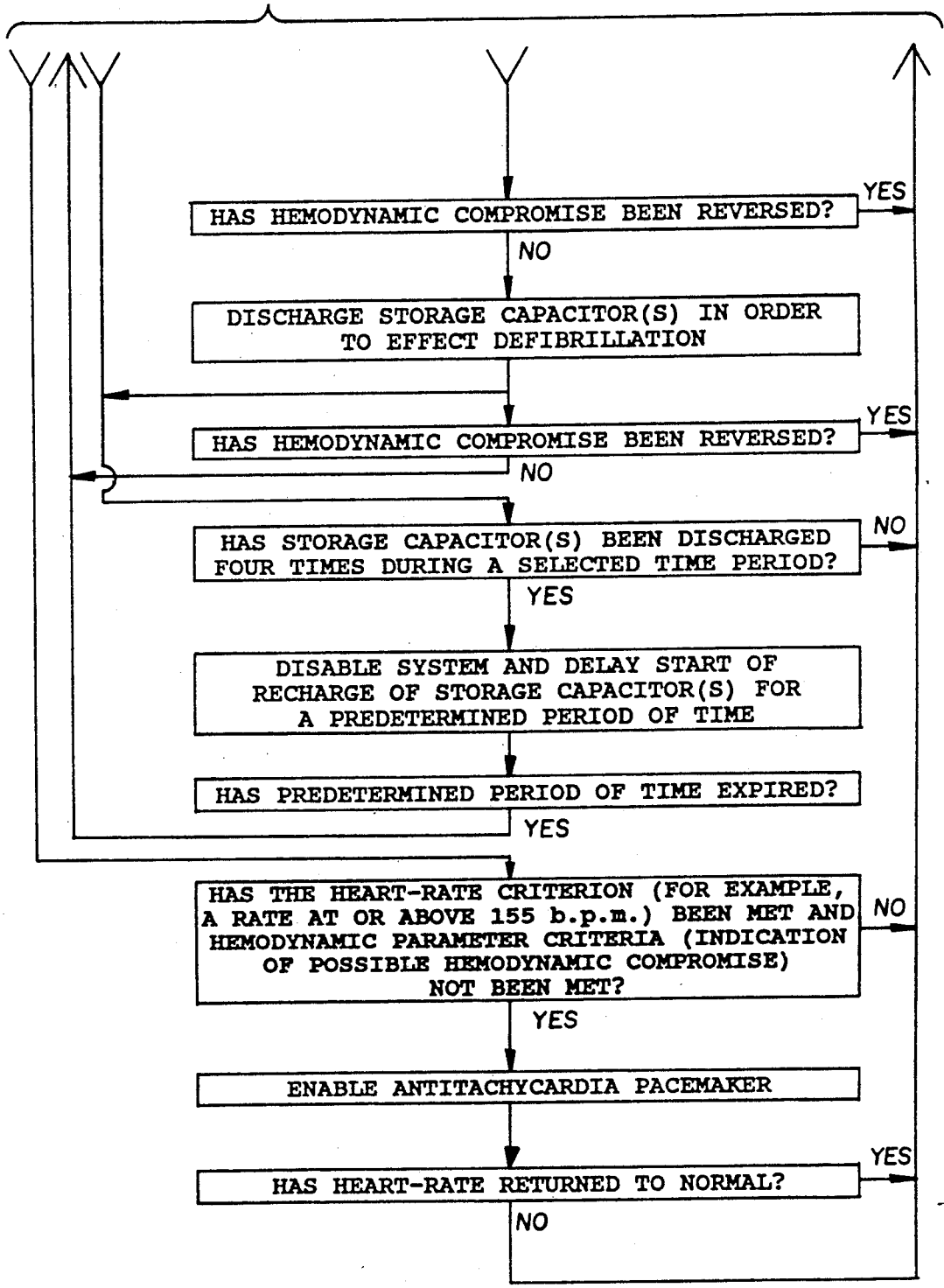

It is to be appreciated that the circuit of FIG. 19 described above may be considered, at least in part, to be a controller processor, which could be realized as a microprocessor, the processor being identified by the numeral 82. The processor 82, with its associated components, in effect carries out the steps set out in the flowchart of FIGS. 20A and 20B.

The circuit of FIG. 19 could be associated with a failsafe antibradycardia pacemaker, if desired.

Figure 10:
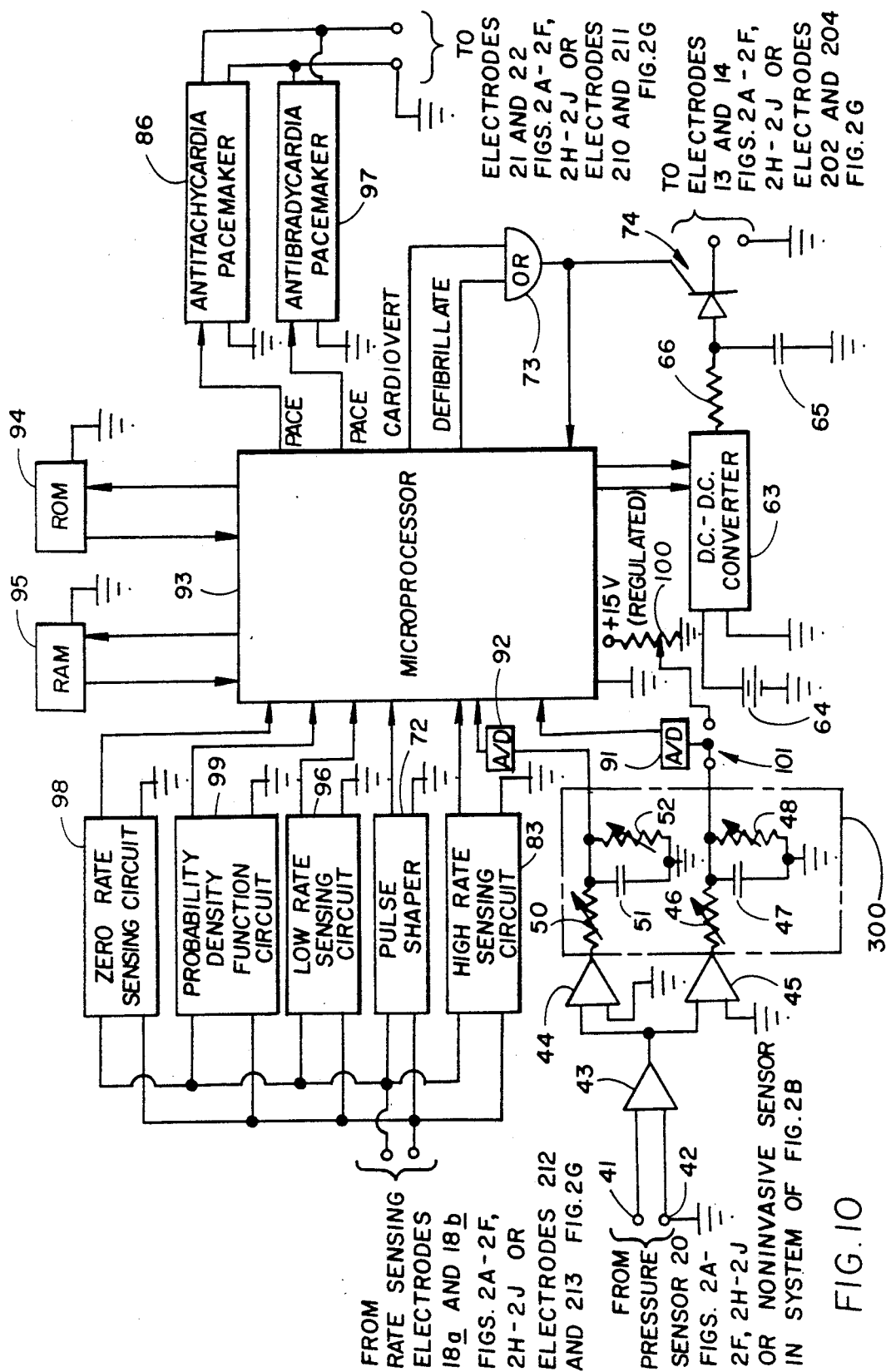
FIG. 10 is a partially block, schematic diagram of a hemodynamically responsive system for treating a malfunctioning heart which provides a microprocessor implementation in accordance with preferred embodiments of the present invention, as well as those illustrated in FIGS. 4, 6 and 8.

Turning to FIG. 10, a fourth exemplary embodiment of circuit components of a system for treating a malfunctioning heart, which may be positioned within the housing 12 (FIGS. 1 and 3) or in the apparatus 208 (FIG. 2G) or used in a portable system which may be carried on the body of a patient or used in fixed installation, such as in ICU's, CCU's, hospital rooms and the like includes a pair of input terminals 41, 42 which receive the variable D.C. voltage output signal representing pressure from the pressure responsive transducer 20 (FIGS. 1, 2A–2F and 2H–2J) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 10 can be used in practicing the present invention using either hemodynamic parameter (such as pressure) criterion alone or both rate and hemodynamic parameter criteria (either in parallel or series). The circuit of FIG. 10 can be used to carry out the methods, illustrated as algorithms in the flowcharts of FIGS. 5A, 5B and 7A, 7B and 9A, 9B, 16A, 16B and 18A, 18B and 20A, 20B. The circuit of FIG. 10 can be considered as a digital, microprocessor-based version of the hand-wired analogue circuitry shown in FIGS. 4, 6 and 8, when the single-pole, double-throw switch 101 is set as shown. In the other position of the switch 101, the circuit can be considered to be a digital, microprocessor-based version of the hand-wired analogue circuitry illustrated in FIGS. 15, 17 and 19. Of course, the microprocessor-based circuit of FIG. 10 could be programmed to carry out other routines. For example, were a heart rate criterion to be satisfied, the circuit could be arranged (1) simply to monitor selected hemodynamic parameter (such as pressure), (2) to effect antitachycardia pacing and/or to cardiovert. As further examples, were both rate and the selected hemodynamic criteria to be satisfied, the circuit of FIG. 10 could be programmed (1) to effect antitachycardia pacing and/or (2) to cardiovert/defibrillate. Moreover, the selected interventions could be programmed so that when one is tried and fails, another is tried and so on. For example, if a tachycardia were detected regardless of whether or not hemodynamic compromise is present an antitachycardia pacemaker would attempt early to revert the arrhythms to normal and if this fails cardioversion/defibrillation would then attempt the same. A detailed discussion of one possible program is discussed below.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage (first signal) across the capacitor 47 represents the mean pressure sensed by the transducer 20 (FIGS. 1, 2A–2F and 2H–2J) or the noninvasive transducer (in system of FIG. 2G) over a relatively long period, for example during the preceding fifteen (15) minutes or even longer (for example a number of hours) of shorter (for example 120 seconds) being suitable in some cases. The D.C. voltage level across the capacitor 47 thus represents a long term mean baseline pressure. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the resistor 51 represents the short term mean pressure sensed by the transducer 20 (FIGS. 1, 2A–2F and 2H–2J) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively via respective analogue-to-digital converters (A/D's) 91 and 92 to respective inputs of a microprocessor 93. The A/D converters 91 and 92, in operation, convert the respective analogue signals which appear across capacitors 47 and 51 into corresponding digital signals for processing by the microprocessor 93, the microprocessor having associated therewith a ROM 94, which supplies programmed instructions to the microprocessor, and a RAM 95, which stores and supplies digital signal representations of pressure-related signals from and to the microprocessor.

Another input of the microprocessor 93 is supplied with high (ONE) and low (ZERO) signals from a high rate sensing circuit 83, which produces a ONE signal whenever the heart rate, as sensed by the electrodes 18a and 18b (FIGS. 2A-2F and 2H-2J) or by the electrodes 212 and 213 (FIG. 2G), exceeds a predetermined rate, for example a rate of 155 b.p.m. The actual rate selected would, of course, depend on the individual patient and a professional opinion as to his or her condition. A pulse shaper 72, which also receives an input from the rate sensing electrodes 18a and 18b (FIGS. 2A-2F and 2H-2J) or from the rate sensing electrodes 212 and 213 (FIG. 2G), is provided to supply narrow D.C. pulses to the microprocessor 93; if present, these pulses would be used as synchronizing pulses for cardioversion.

An antitachycardia pacemaker 86 is connected to an output terminal of the microprocessor 93 to receive therefrom a pace enable signal to, in effect, enable or turn on the pacemaker 86 under the command of the microprocessor 93. Two other output terminals from the microprocessor 93 provide respective cardiovert and defibrillate command signals to an OR circuit 73, which cooperates with a D.C.-to-D.C. converter 63, a battery 64, a charging resistor 66, storage capacitor 65 and a SCR 74 in the same manner as the corresponding circuit components having the same reference numerals function in the hand-wired circuits illustrated in FIGS. 4, 6 and 8. The output of the OR gate 73 is also supplied to an input terminal of the microprocessor 93, supplying signals to a counting means within the microprocessor 93 which corresponds to the counter 81 (FIGS. 4, 6 and 8).

As thus far described, the circuit of FIG. 10 can carry out the methods defined in the flowcharts of FIGS. 5A, 5B and 7A, 7B and 9A, 9B, the respective programs being supplied by the ROM 94. In operation, the circuit of FIG. 10, with the switch 101 set as illustrated, can be seen as a microprocessor realization of the hand-wired analogue circuits of FIGS. 4, 6 and 8. With the switch 101 set in its other position, the capacitor 47 and the resistor 48 are disconnected from the input to the A/D converter 91 and the wiper of the potentiometer 100 connected thereto. The voltage which appears on the wiper of the potentiometer 100 thus constitutes the first signal, representing in this case the fixed baseline pressure. The circuit of FIG. 10 when so connected on a carry out the methods defined in the flowcharts of FIGS. 16A, 16B and 18A, 18B and 20A, 20B. It is to be appreciated that the circuit of FIG. 10 can be programmed to effect somewhat different routines and be provided with additional inputs, as well.

If desired for example, a low rate sensing circuit 96 could be provided, its input being coupled to the rate sensing electrodes 18a and 18b (FIGS. 2A-2F and 2H-2J) or the rate sensing electrodes 212 and 213 (FIG. 2G). The low rate sensing circuit 96 supplies a high (ONE) signal to an input terminal whenever the beating rate, as sensed by the electrodes 18a and 18b or the electrodes 212 and 213, falls below a given rate, for example 45 b.p.m., indicative of bradycardia. Under these conditions (provided the rate were not zero), the microprocessor 93 would provide a command enable signal to an antibradycardia pacemaker 97. When enabled, the pacemaker 97 would supply bradycardia-correcting pacing signals to a patient's heart via the pacing electrodes 21 and 22 (FIGS. 1, 2A-2F and 2H-2J) or the pacing electrodes 210 and 211 (FIG. 2G).

If desired, a zero rate sensing circuit 98, responsive to output from the rate sensing electrodes 18a and 18b (FIGS. 2A-2F and 2H-2J) or the rate sensing electrodes 212 and 213 (FIG. 2G) can be provided. This zero rate sensing circuit 98 produces a high (ONE) output signal whenever the beating rate is zero, indicating the heart has stopped beating (sometimes referred to as going "flat line"). This may represent either asystole or fine ventricular fibrillation. Under this condition, the microprocessor 93 is programmed to first effect a charging and discharging of the storage capacitor 65, supplying a ONE signal via its command defibrillate output connection to the OR gate 73 and then to effect antibrachycardia pacemaking after a given number of capacitor(s) discharges (say 4) if no hemodynamic improvement is noted. The order of defibrillation and pacemaking may be programmed in a reverse manner as desired.

The circuit of FIG. 10 includes, if desired, a narrow window probability density function circuit 99, which has its input coupled to the sensing electrodes 18a and 18b or sensing electrodes 212 and 213. The probability density function circuit may be of the type disclosed in U.S. Pat. Nos. 4,184,493, 4,202,340 and 4,475,551 of Langer et al. and which produce a high (ONE) output signal whenever fine ventricular fibrillation is present. This ONE output is supplied to an input of the microprocessor 93 which, in accordance with its program stored in the ROM 94, effects the charging and discharging of the storage capacitor 65, supplying via its command defibrillate output a ONE signal to the OR gate 73 to initiate discharge.

Conventional antitachycardia systems function primarily as rate-only sensing devices and perform inadequately in differentiating hemodynamically stable from unstable tachycardias. Consequently, in the course of developing the present invention, mean right atrial (MRAP), mean right ventricular (MRVP), and mean arterial pressures (MAP) were studied by the applicant for determining if a basis was present to distinguish significant arrhythmias and serve as a basis for improving antitachycardia systems.

Hemodynamic responses to rapid atrial and ventricular pacing were examined in 10 closed-chest anesthetized dogs. Pressure monitoring catheters placed in the femoral artery, high right atrium (HRA), and right ventricular apex (RVA) measured MAP, MRAP, and MRVP at baseline heart rates and after 30 and 60 sec. rapid HRA and RVA pacing. Pressures recorded during rapid pacing (average of the pressures at 30 and 60 sec. of pacing) at pacing rates of 180, 250, and 280/min. were compared to those recorded initially at baseline heart rates.

Figure 11:
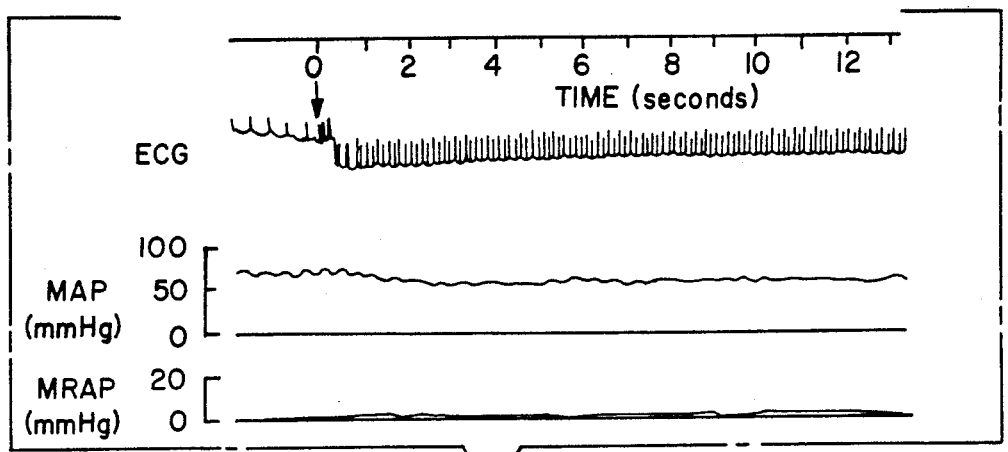
FIGS. 11-13 are respective graphical representations along a time axis of a rate wave (R-wave), mean arterial pressure (MAP) and mean right atrial pressure (MRAP) of a canine subject respectively under high right atrial pacing, right ventricle apex pacing and in ventricular fibrillation, useful in understanding the present invention.
Figure 12:
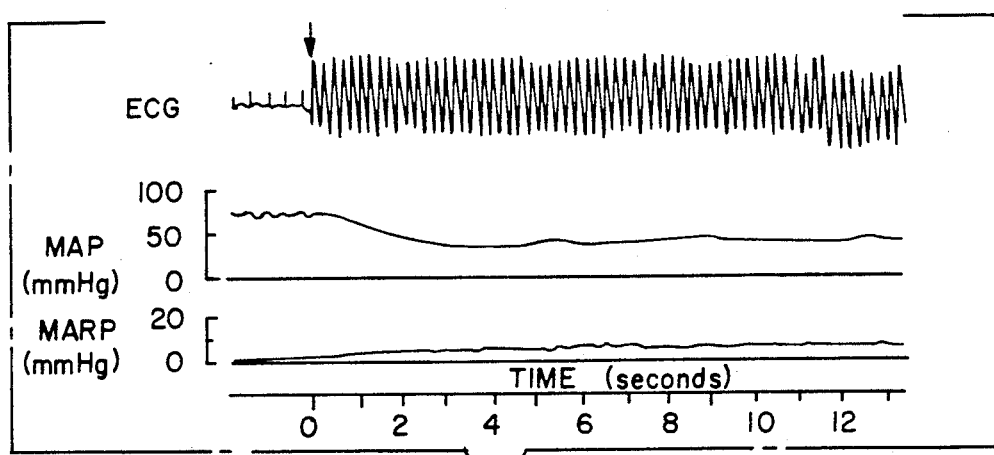
Figure 13:
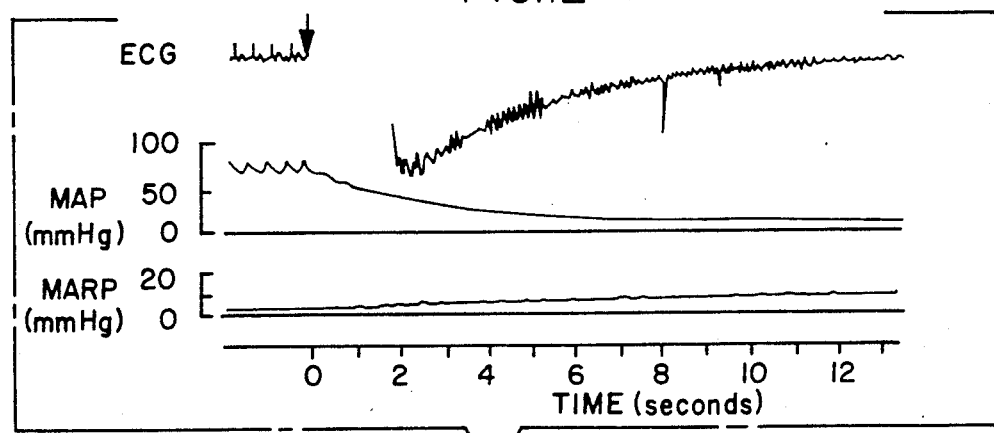
Figure 14:
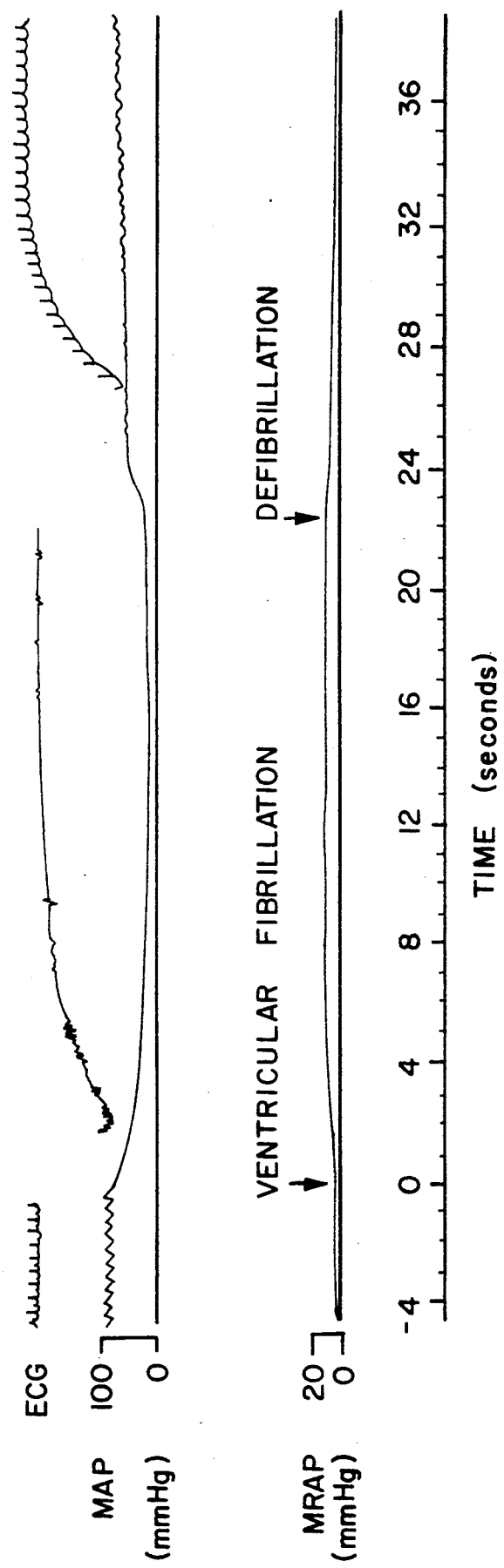
FIG. 14 is a graphical representation along a time axis similar to the graphical representation of FIG. 13, the time base having been expanded to show the affects on the R-wave, the MAP and MRAP which result from successful defibrillation.

An exemplary graphical representation of the ECG wave MAP and MRAP of one dog is illustrated in FIG. 11 along a time base of 15 seconds, the pacing rate in this case being 250 b.p.m. starting at time zero. The traces of MAP and MRAP indicate that the changes are slight; hemodynamic compromise is not indicated. As illustrated in FIG. 12, when the dog was subjected to a pacing rate of 280 b.p.m. starting at time zero, in this case as clearly shown by the traces, the MAP dropped markedly within two seconds and MRAP increased markedly within one second. Hemodynamic compromise prevailed. Thus, it is clear that the selected criteria can be sensed and properly form the basis of improved antitachycardia systems and methods. In FIG. 13, traces of MAP and MRAP of a dog whose heart has been placed in ventricular fibrillation at time zero clearly shows marked hemodynamic compromise, the traces of the MAP and MRAP indicating that MAP dropped and continued to drop to an extremely low level in about eight seconds, while the MRAP increased considerably within the same period. As sensing algorithms, a MRAP algorithm and a combined MRAP-rate algorithm were tested in this dog using a hand operated antitachycardia-defibrillator system. In FIG. 14, the ECG, MAP and MRAP traces of a dog whose heart was placed into ventricular fibrillation at time zero is shown for a time period of about 36 seconds, a defibrillating pulse having been applied after a time lapse of about 22 seconds. As shown in the MAP and MRAP traces of FIG. 14, considerable hemodynamics comprise appears from the onset of fibrillation and once the defibrillating pulse has been applied, is reversed. Moreover, normal beating rate was restored within about three seconds.

Rapid RVA pacing, simulating ventricular tachycardia, resulted in significant increases in MRAP and MRVP with marked hemodynamic compromise. These parameters remained stable during HRA pacing (simulating atrial tachycardia). The sensing algorithms successfully indicated those arrhythmias requiring termination, hemodynamically unstable ventricular tachycardia and fibrillation. Hemodynamically stable tachycardias were merely monitored, not manually terminated.

Thus, one can conclude that MRAP, MRVP and MAP, as well as other mean pressures, are useful in distinguishing hemodynamically significant tachycardias and could be used a sensed parameters in hemodynamically responsive antitachycardia systems.

The respective hemodynamic systems for treating a malfunctioning heart and which respond to a selected hemodynamic parameter include a signal processing circuit generally designated by the numeral 300 in FIGS. 4, 6 and 8. As shown, the signal processing circuit 300 derives long and short term mean pressures. Were a different hemodynamic parameter, such as systolic pressure, diastolic pressure, diastolic end pressure or pulse pressure selected, different signal processing circuits may be used, as replacements. Such circuits are illustrated respectively in FIGS. 21, 22, 23 and 24A, 24B. In each case, the rate-of-change in these particular parameters could be determined.

Figure 21:
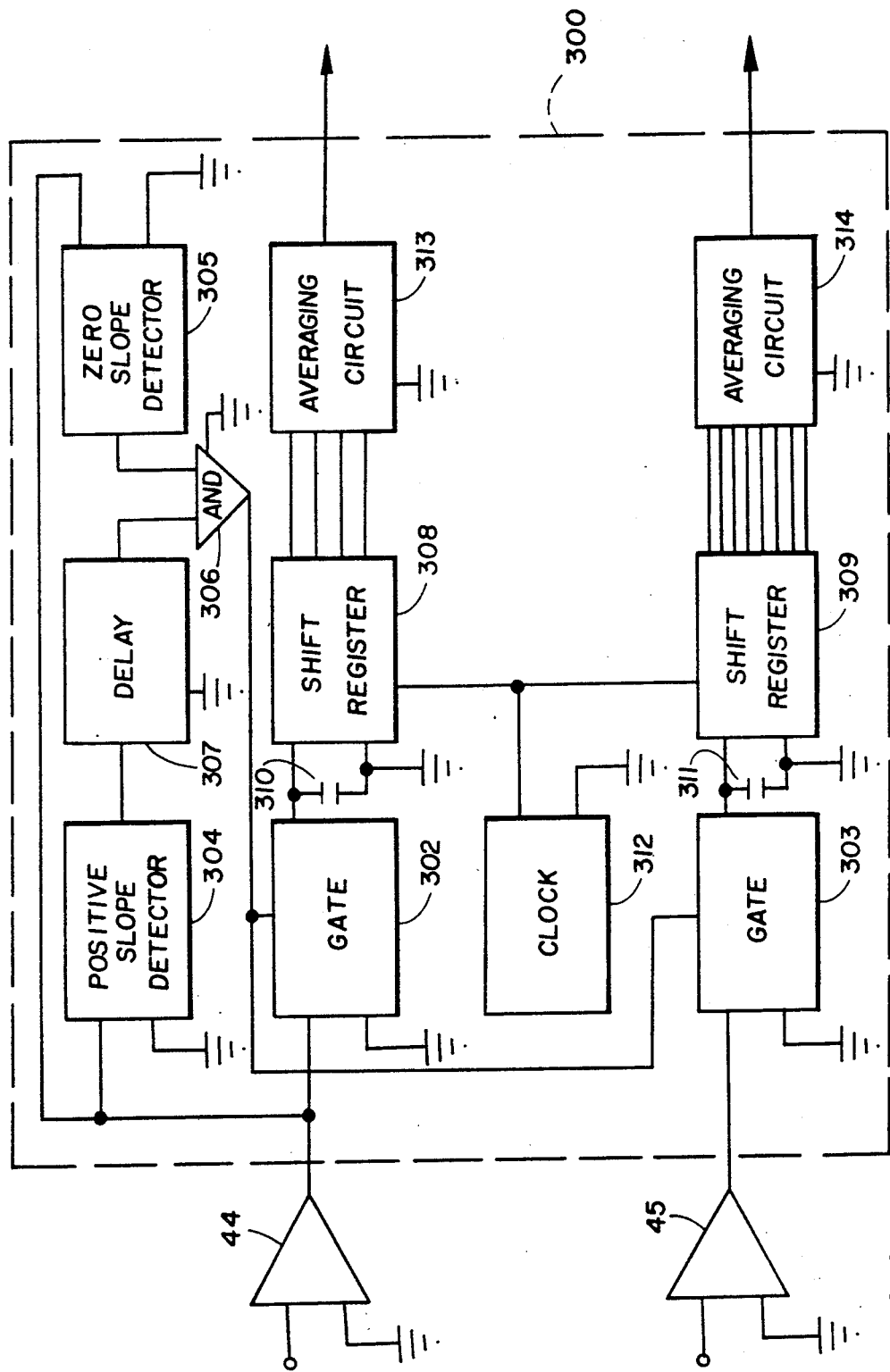
FIGS. 21-23 and 24A, 24B are respective simplified block diagrams of signal processing circuits which may be used in the circuits to determine respectively RVSP, RVDP, RVEDP and RVPP.

Turning to FIG. 21, the replacement signal processing circuit 300, shown associated with amplifiers 44, 45 (also shown in FIGS. 4, 6 and 8). The pressure sensor 20, positioned as shown in FIG. 2A, would be used to develop a pressure-responsive signal which would, after amplification in preamplifier 43 (FIGS. 4, 6 and 8), be amplified in the respective amplifiers 44 and 45 and supplied as signal inputs to respective gates 302 and 303. The output signal from the amplifier 44 is also fed to positive slope detector 304 and to zero slope detector 305. Output from the respective detectors 304 and 305 are fed to an AND circuit 306, the positive slope detector being coupled to the AND circuit 306 via a delay circuit 307.

The output from the AND circuit 306 is fed to the enabling inputs of the gates 302 and 303. Output from the gates 302 and 303 are fed to respective shift registers 308 and 309, respective signal storage being provided by storage means, shown diagrammatically as respective capacitors 310, 311. A clock 312 is provided for shifting signals provided from the gates 302 and 303 into and through the respective shift registers 308 and 309.

Signals from the individual stages of the respective shift registers 308 and 309 are fed in parallel to respective arithmetical averaging circuits 313 and 314.

In operation, respective electrical signals representations of RVP are fed to the gates 302, 303. So long as the slope of the output signal from the amplifier 44 is positive, indicating an increasing instant pressure within the right ventricle, a ONE output, delayed slightly appears as a ONE signal on an input to the AND gate 306. So long as the zero slope detector 305 does not detect a zero slope in the signal received from the amplifier 44, which would otherwise be present were the systolic pressure peak present, a ZERO would appear on the second input to the AND gate 306. When a zero slope condition is detected the second input to the AND gate 306 becomes ONE and a ONE appears on the output of the AND gate.

The ONE output from the AND gate 306 enables each of the gates 302 and the current signal level outputs, actual real time representation of peak pressure, from the respective amplifier 44, 45 are supplied to the respective gates 302 and 303 and temporarily stored in storage members, shown diagrammatically as the capacitors 310 and 311. The stored levels are gated into the respective shift registers 308 and 309 and stepped through the stages within the registers under control of the clock 312. The shift register 309 has relatively more stages than the shift register 308 so that long term data is present in register 309 at any given time and short term data is present in register 308, and the respective averaging circuits 314 and 313 produce outputs representing respectively long term and short term signal representations of RVSP. Output from the respective arithmetical averaging circuits 313 and 314 are supplied to other circuit components of the systems shown in FIGS. 4, 6 and 8 in place of the signals appearing across the respective RC circuits 51, 52 (FIGS. 4, 6 and 8) and 47, 48 (FIGS. 4, 6 and 8).

Figure 22:
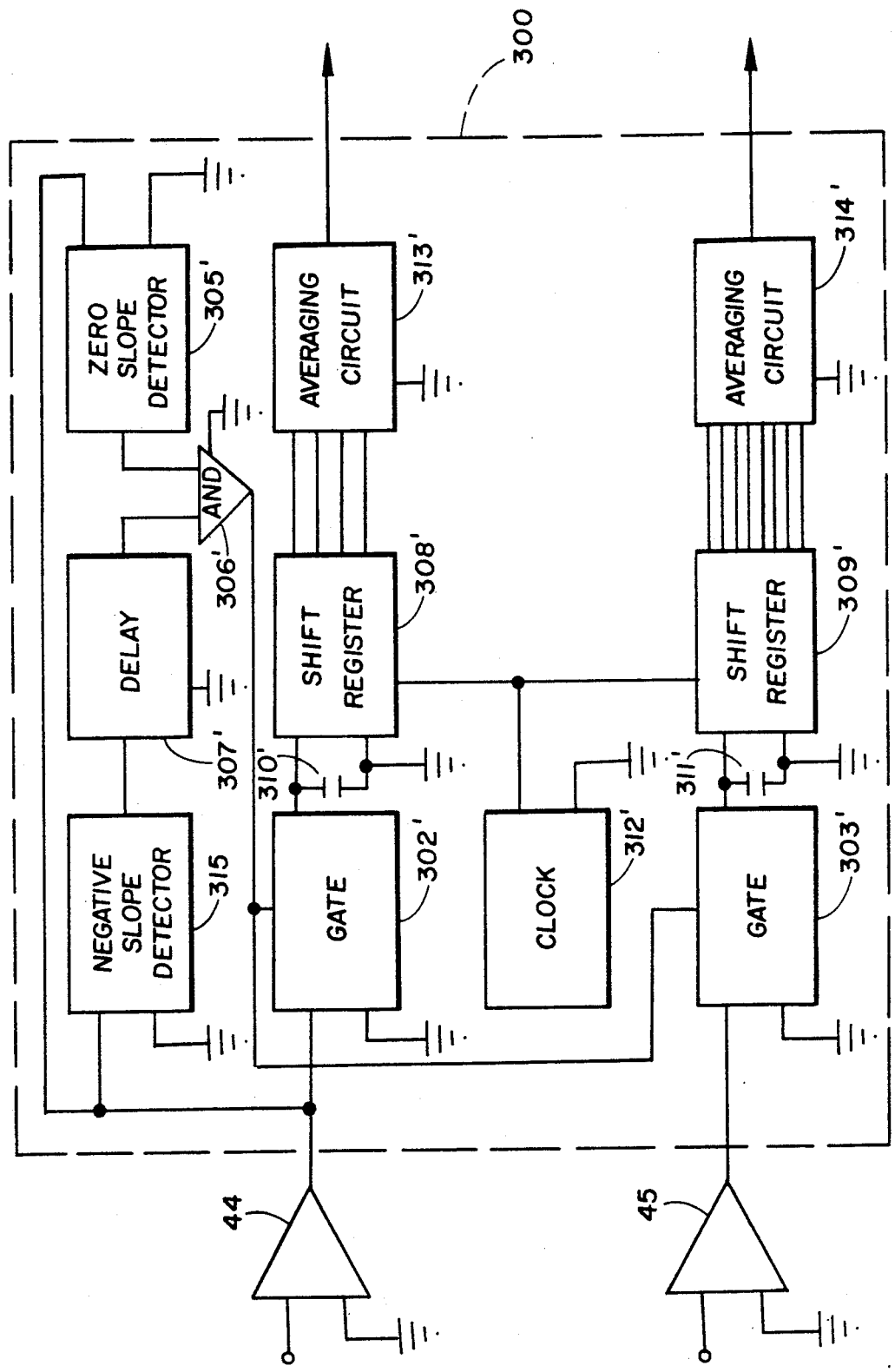

Were one to wish to use right ventricular diastolic pressure (RVDP) as the selected hemodynamic parameter, the circuit of FIG. 22 could be used as the signal processing circuit. The circuit of FIG. 22 differs from the circuit of FIG. 21 only in that a negative slope detector 315 has been substituted for the positive slope detector 304 (FIG. 21). The remaining circuit components are the same, albeit these components are designated by numerals associated with a prime (') sign.

Figure 23:
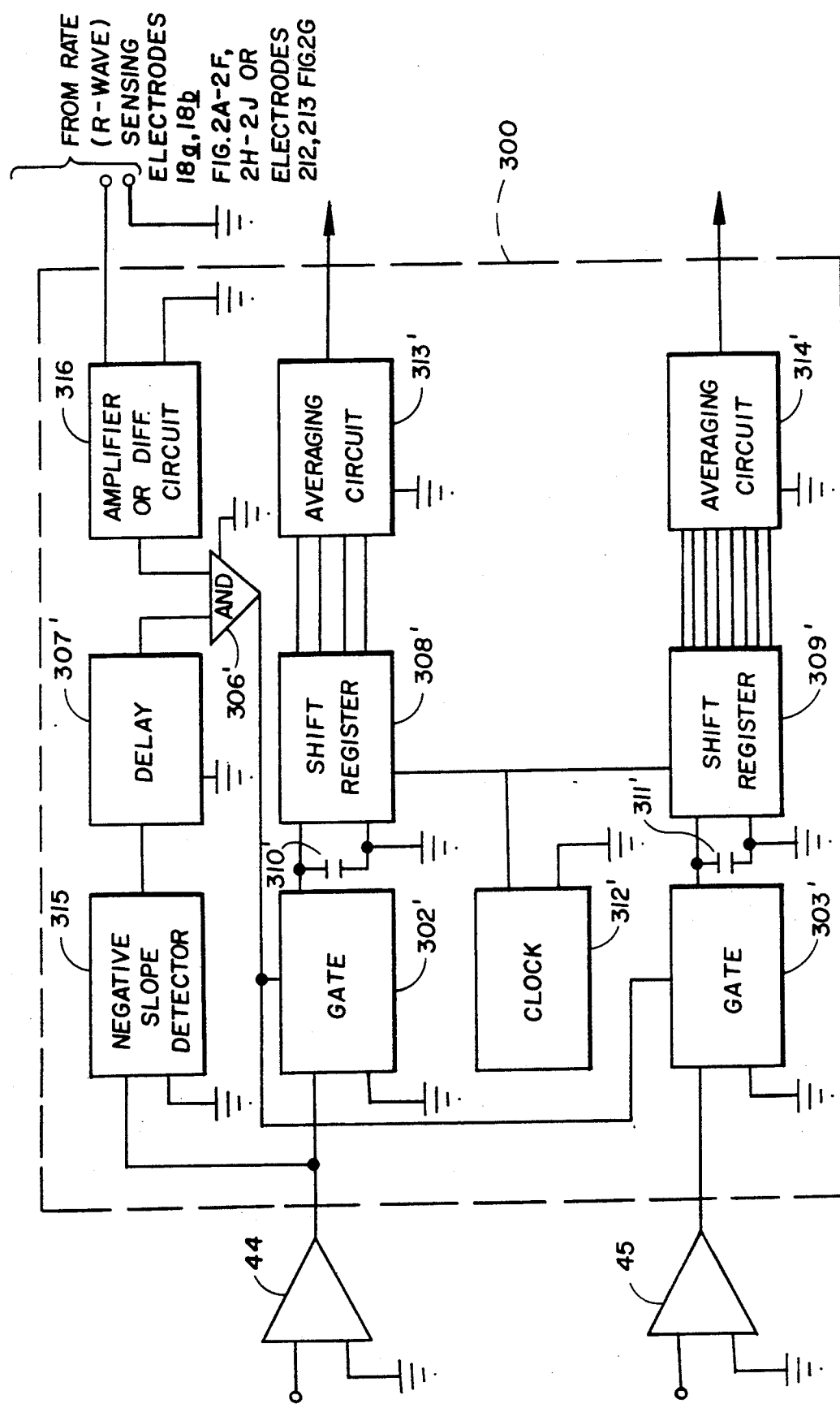

Were one to select right ventricular end diastolic pressure (RVEDP) as the hemodynamic parameter, the circuit shown in FIG. 23 could be used. In this case, the zero slope detector 305 (FIG. 22) would be replaced by an amplifier or differentiating circuit 316 which receives its input from the R-wave sensing electrodes so that the output from the AND circuit 306 would be ONE only when a delayed output signal from the negative slope detector 315 and a signal from the amplifier 316, indicative of the occurrence of an R-wave peak, or the appearance of the leading edge of the R-wave were one to elect to use a differentiating circuit as the circuit component 316.

Figure 24A:
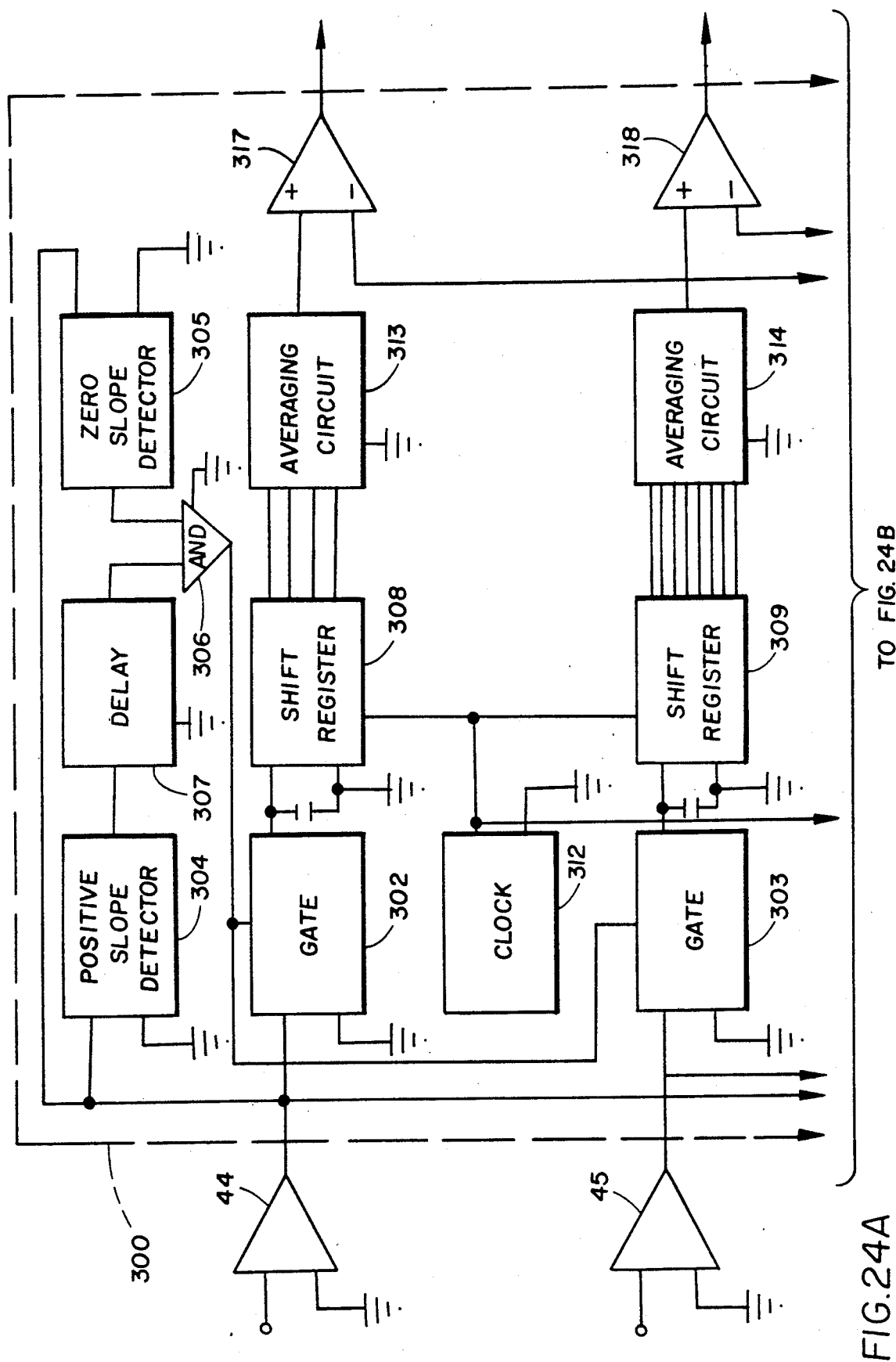
Figure 24B:
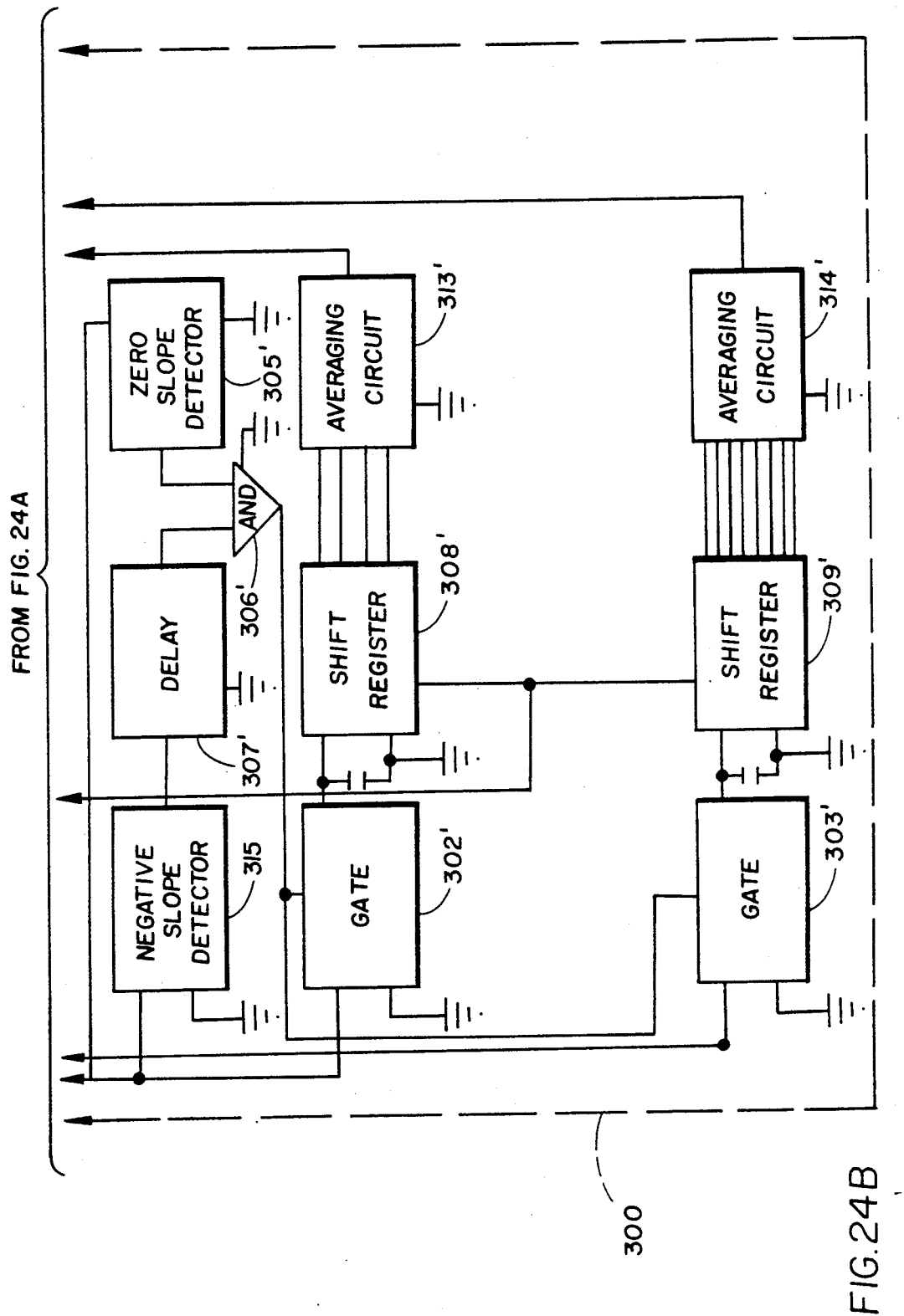

Were right ventricular pulse pressure (RVPP) to be the selected hemodynamic parameter, the circuit of FIGS. 24A, 24B could be used. The circuit of FIGS. 24A, 24B is, in essence, a combination of the circuits of FIGS. 22 and 23, with two operational amplifiers 317 and 318 added between the the averaging circuits and the remaining circuitry of FIGS. 4, 6 and 8. As shown in FIGS. 24A, 24B, outputs from the respective averaging circuits 313 and 313' are fed respectively to the noninverting and inverting inputs of the operational amplifier 317 which produces, as its output, a signal representation of the difference between the short term RVSP and the short term RVDP. Similarly, output from the respective averaging circuits 314 and 314' are fed to the respective noninverting and inverting inputs of the operational amplifier 318 which produces a signal representing the difference between long term RVSP and long term RVDP. The circuits of FIGS. 21, 22, 23 and 24A, 24B could also be used as a replacement for the circuit 300 in the system of FIG. 10.

In the event one wished to apply the teachings of FIGS. 21, 22, 23 and 24A, 24B to the fixed (possibly adjustable) baseline, the portion of the circuits of FIGS. 21, 22, 23 and 24A, 24B involving the short term determinations would be retained and used as replacements for the signal processing circuit 301 shown in FIGS. 15, 17 and 18.

Figure 25:
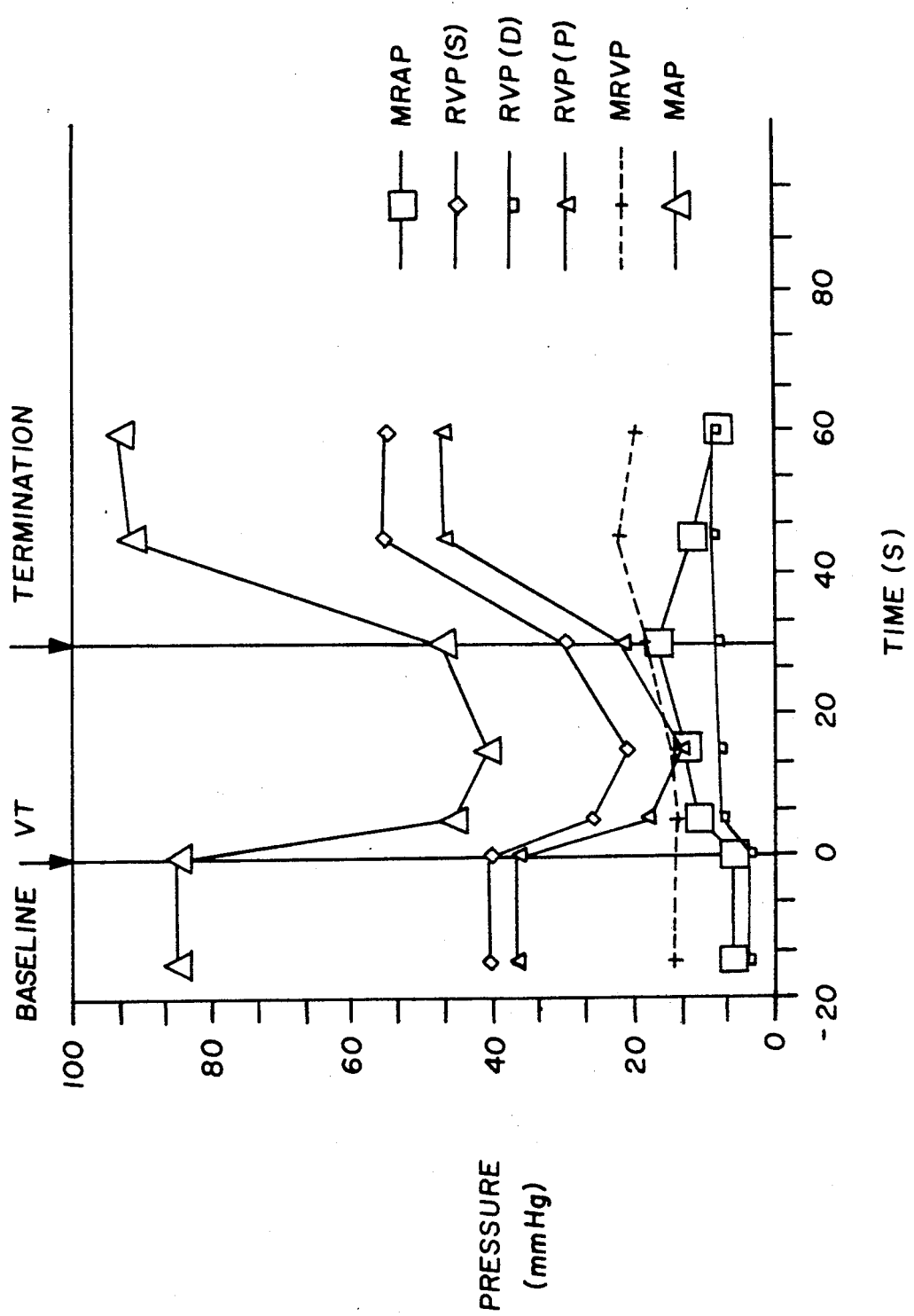
FIG. 25 is a graphical representation useful in understanding the present invention which shows the respective variations of hemodynamic parameters, in particular pressure parameters, collected during a study of a number of patients, the graphic representations of MAP, RVSP and RVPP showing the distinct dP/dt relationship during hemodynamic compromise.

The hemodynamic responses to the onset and termination of sustained ventricular tachyarrhythmias were further studied by applicant and his coworkers in 20 human patients to determine the ideal parameter(s) for a hemodynamically responsive antitachycardia system. Right atrial, right ventricular, and mean arterial pressures along with intracardiac electrograms were continuously recorded. Patients were $57 \pm 3$ years (mean$\pm$SE) with an average left ventricular ejection fraction of $28 \pm 3\%$. The underlying heart disease was coronary artery disease with a remote myocardial infraction (15 patients), cardiomyopathy (4 patients), and Ebstein's anomaly (1 patient). As illustrated graphically in FIG. 25, pressures were measured at baseline (cycle length of $701 \pm 30$ ms); at 5, 15, and 30 seconds after ventricular tachyarrhythmia induction (19 ventricular tachycardias and 4 ventricular fibrillations; cycle length of $247 \pm 11$ ms); and at 15 and 30 seconds after arrhythmia termination (cycle length of $688 \pm 30$ ms). At 15 seconds of tachyarrhythmia, when mean arterial pressure (MAP) decreased from baseline $80 \pm 4$ mmHg to $34 \pm 3$ mmHg, mean right atrial pressure (MRAP) increased from baseline $7 \pm 1$ mmHg to $14 \pm 1$ mmHg. Right ventricular systolic pressure (RVSP) decreased from $39 \pm 2$ mmHg to $27 \pm 2$ mmHg, but right ventricular diastolic pressure (RVDP) increased from $7 \pm 1$ mmHg to $11 \pm 1$ mmHg, resulting in a right ventricular pulse pressure (RVPP) decrease from $32 \pm 3$ mmHg to $13 \pm 2$ mmHg; all changes from baseline were significant at 95% by the Dunnett's test. Changes in mean right ventricular pressure (MRVP) during this study did not appear to be as significant, as are other pressure changes, and is not now recommended as a preferred parameter. The changes persisted throughout the 30 seconds of ventricular tachyarrhythmias. Change in right ventricular end diastolic pressure (RVEDP) upon termination, all pressures except mean right ventricular pressure and right ventricular diastolic pressure returned rapidly towards baseline. In conclusion, mean arterial pressure (MAP), mean right atrial pressure (MRAP), right ventricular systolic pressure (RVSP) and pulse pressure (RVPP) appear useful parameters for sensing and determining as hemodynamic parameters for incorporation into the algorithms of a cardioverter-defibrillator and antitachycardia devices, in general, and in particular the present invention.

The present invention provides significant advancements in the treatment of patients having malfunctioning hearts. The systems of the present invention operate automatically. The baseline pressure and permitted deviations therefrom are not based on an average of a large sampled population or standard; rather, these parameters are patient-specific.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. In a cardioverting/defibrillation system for treating a malfunctioning heart of the type which includes storage means for storing electrical energy, electrode means for electrically coupling the storage means to the heart, sensing means for sensing pressure at least one site within a circulatory system of an individual, means responsive to output from the sensing means for developing a first signal representing current level of the pressure over a period of predetermined duration, means responsive to the first signal for determining rate of change of the first signal and algebraic sign of the rate of change, and means responsive to output from the means responsive to the first signal for charging and enabling discharge of the electrical energy stored by the storage means across the electrode means upon the rate of change of the first signal exceeding a predetermined amount and being of a given algebraic signal.

2. The system according to claim 1, wherein the means for developing a first signal representative of current level of the pressure comprise means providing a signal representative of current mean arterial pressure within the circulatory system of an individual.

3. The system according to claim 1, wherein the means for developing a first signal representative of current level of the pressure comprises means providing a signal representative of current right ventricular systolic pressure.

4. The system according to claim 1, wherein the means for developing a first signal representative of current level of the pressure comprise means providing a signal representing current right ventricular pulse pressure.

5. The system according to claim 1, wherein the means for developing a first signal representative of current level of the pressure comprises means for providing a signal representative of current systolic pressure at the site within the circulatory system of an individual.

6. The system according to claim 1, wherein the means for developing a first signal representation of current level of the pressure comprises means for providing a signal representative of pulse pressure at the site within the circulatory system of an individual.

7. The system according to claim 1, wherein the means responsive comprises a microprocessor for developing a control signal to control the means for charging and enabling discharge of the electrical energy stored by the storage means.

8. The system according to claim 1, including electrical means for sensing heart rate and producing a distinctive control signal upon the heart rate exceeding a predetermined rate, controllable antitachycardia pacemaking means for supplying pacing signals to the heart, controllable cardioverting/defibrillating means, including the storage means for storing electrical energy, control circuit means responsive to the distinctive control signal and to an output from the means for charging and enabling discharge to enable the antitachycardia pacemaking means in response to presence of the distinctive control signal and contemporaneous absence of the output and for enabling said cardioverting/defibrillating means in response to contemporaneous presence of both the distinctive control signal and the output.

9. The system according to claim 8, including means responsive to output from said electrical means for sensing heart rate for developing a discharge-synchronizing signal synchronized to an R-wave, and the means for discharging electrical energy across the electrode means and into the heart includes means for synchronizing the discharge with the discharge-synchronizing signal to effect cardioversion.

10. The system according to claim 9, wherein the means for discharging electrical energy across the electrode means and into the heart effects discharge on a nonsynchronized basis, in the absence of the discharge-synchronizing signal, to effect defibrillation.

11. The system according to claim 1, including means for discharging electrical energy across said electrode means and into the heart effects discharge on a nonsynchronized basis to effect defibrillation.

12. A method of treating a malfunctioning heart comprising providing a representation of a pressure parameter at a least, one site in a circulatory system for an individual determining current level of the pressure parameter over a period of given duration, determining rate of change and algebraic sign thereof in the current level, and delivering cardioverting/defibrillating electrical energy to the heart whenever the rate of change exceeds a predetermined amount and the sign thereof is a given algebraic sign.

13. The method according to claim 12, wherein the step of determining is constituted by determining pulse pressure at the site in the circulatory system of an individual.

14. The method according to claim 12, wherein the step of determining is constituted by determining right ventricular pulse pressure.

15. The method according to claim 12, wherein the step of determining is constituted by determining systolic pressure at the site in the circulatory system of an individual.

16. The method according to claim 12, wherein the step of determining is constituted by determining right ventricular systolic pressure.

17. The method according to claim 12, wherein the step of determining is constituted by determining mean arterial pressure at the site in the circulatory system of an individual.

18. The method according to claim 12, including sensing heart rate, the step of delivering cardioverting/defibrillating electrical energy being taken upon the heart rate exceeding a given rate and the rate of change in the current level exceeding the predetermined amount and being of the given algebraic sign.

19. A cardioverting/defibrillating system for treating a malfunctioning heart comprising means for determining rate of change and algebraic sign thereof in at least one current pressure parameter at a site in a circulatory system of an individual and means responsive to output from the determining means for providing an output to overcome the malfunction upon the rate of change of the pressure parameter exceeding a predetermined amount and the sign thereof being a given algebraic sign.

20. In a cardioverting/defibrillating system for treating a malfunctioning heart of the type which includes storage means for storing electrical energy to be used to effect cardioversion/defibrillation, electrode means for electrically coupling the storage means to the heart, sensing means for sensing at least one hemodynamic parameter at a least one site within a circulatory system of an individual, means responsive to output from the sensing means for developing a first signal representing current level of the hemodynamic parameter over a period of predetermined duration, means responsive to the first signal for determining rate of change of the first signal and algebraic sign of the rate of change, and means responsive to output from the means responsive to the first signal for charging and enabling discharge of the electrical energy stored by the storage means across the electrode means to effect cardioversion/defibrillation upon the rate of change of the first signal exceeding a predetermined amount and being of a given algebraic sign.

21. The system according to claim 20, wherein the means for developing a first signal representative of current level of the hemodynamic parameter comprises means providing a signal representative of current means pressure at the site within the circulatory system of an individual.

22. The system according to claim 20, wherein the means for developing a first signal representative of current level of the hemodynamic parameter comprises means providing a signal representative of current systolic pressure at the site within the circulatory system of an individual.

23. The system according to claim 20, wherein the means for developing a first signal representative of current level of the hemodynamic parameter comprises means providing a signal representing current pulse pressure at the site within the circulatory system of an individual.

24. The system according to claim 20, wherein the means for developing a first signal representative of current level of the hemodynamic parameter comprises means providing a signal representative of current pressure at the site within the circulatory system of an individual.

25. The system according to claim 20, wherein the means responsive comprises a microprocessor for developing a control signal to control the means for charging and enabling discharge of the electrical energy stored by the storage means.

26. The system according to claim 20, including electrical means for sensing heart rate and producing a distinctive control signal upon the heart rate exceeding a predetermined rate, controllable antitachycardia pacemaking means for supplying pacing signals to the heart, controllable cardioverting/defibrillating means, including the storage means for storing electrical energy, control circuit means responsive to the distinctive control signal and to an output from the means for charging and enabling discharge to enable the antitachycardia pacemaking means in response to presence of the distinctive control signal and contemporaneous absence of the output and for enabling said cardioverting/defibrillating means in response to contemporaneous presence of both the distinctive control signal and the output.

27. The system according to claim 26, including means responsive to output form said electrical means for sensing heart rate for developing a discharge-synchronizing signal synchronized to an R-wave, and the means for discharging electrical energy across the electrode means and into the heart includes means for synchronizing the discharge with the discharge-synchronizing signal to effect cardioversion.

28. The system according to claim 27, wherein the means for discharging electrical energy across the electrode means and into the heart effects discharge on a nonsynchronized basis, in the absence of the discharge-synchronizing signal, to effect defibrillation.

29. The system according to claim 20, including means for discharging electrical energy across said electrode means and into the heart effects discharge on a nonsynchronized basis to effect defibrillation.

30. A method of cardioverting/defibrillating a malfunctioning heart comprising providing a representation of a hemodynamic parameter at least one site in a circulatory system of an individual, determining current level of the parameter over a period of given duration, determining rate of change of the current level and algebraic sign thereof, and delivering stored cardioverting/defibrillating electrical energy to the heart whenever the rate of change exceeds a predetermined amount and is of a given algebraic sign.

31. The method according to claim 30, wherein the step of determining is constituted by determining pulse pressure at the site in the circulatory system of an individual.

32. The method according to claim 30, wherein the step of determining is constituted by determining systolic pressure at the site in the circulatory system of an individual.

33. The method according to claim 30, wherein the step of determining is constituted by determining means pressure at the site in the circulatory system of an individual.

34. The method according to claim 30, including sensing heart rate, the step of delivering cardioverting/defibrillating electrical energy being taken upon the heart rate exceeding a given rate and the rate of change in the current level of the hemodynamic parameter exceeds the predetermined amount and is of the given sign.

* * * * *